United States Patent
Mori et al.

(10) Patent No.: US 9,044,145 B2
(45) Date of Patent: Jun. 2, 2015

(54) PULSE WAVE ANALYSIS DEVICE AND RECORDING MEDIUM

(75) Inventors: Naoki Mori, Takatsuki (JP); Toshihiko Ogura, Inuyama (JP); Kazunobu Itonaga, Takatsuki (JP); Shozo Takamatsu, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 810 days.

(21) Appl. No.: 13/310,421

(22) Filed: Dec. 2, 2011

(65) Prior Publication Data

US 2012/0095353 A1   Apr. 19, 2012

Related U.S. Application Data

(63) Continuation of application No. PCT/JP2010/069093, filed on Oct. 27, 2010.

(30) Foreign Application Priority Data

Oct. 30, 2009  (JP) .................................. 2009-250928

(51) Int. Cl.
    *A61B 5/0285*   (2006.01)
    *A61B 5/02*     (2006.01)
    *A61B 5/021*    (2006.01)
    *A61B 5/0295*   (2006.01)
    *G06F 19/00*    (2011.01)
    (Continued)

(52) U.S. Cl.
    CPC ......... *A61B 5/02007* (2013.01); *A61B 5/02028* (2013.01); *A61B 5/02125* (2013.01); *A61B 5/0295* (2013.01); *A61B 5/0535* (2013.01); *G06F 19/3418* (2013.01); *G06F 19/3431* (2013.01); *A61B 5/7242* (2013.01)

(58) Field of Classification Search
    CPC ... A61B 5/02; A61B 5/02007; A61B 5/02108
    USPC .......................................... 600/490, 500–509
    See application file for complete search history.

(56) References Cited

U.S. PATENT DOCUMENTS

| | | | |
|---|---|---|---|
| 2003/0114764 A1* | 6/2003 | Masuda et al. | 600/490 |
| 2003/0130578 A1* | 7/2003 | Narimatsu | 600/438 |
| 2003/0158488 A1* | 8/2003 | Narimatsu et al. | 600/490 |

(Continued)

FOREIGN PATENT DOCUMENTS

| | | |
|---|---|---|
| JP | A-10-328150 | 12/1998 |
| JP | A-2001-128946 | 5/2001 |

(Continued)

OTHER PUBLICATIONS

International Search Report issued in International Application No. PCT/JP2010/069093 on Nov. 22, 2010 (with translation).

*Primary Examiner* — Navin Natnithithadha
*Assistant Examiner* — Meredith Weare
(74) *Attorney, Agent, or Firm* — Oliff PLC

(57) ABSTRACT

A pulse wave analysis device stores a pulse waveform for multiple beats, and calculates a pulse wave analysis index by analyzing the pulse waveform. In the calculation of the pulse wave analysis index, pulse waveform shapes of each beat that constitute the pulse waveform for multiple beats are integrated, and beats for which a degree of approximation between the integrated pulse waveform shape and the pulse waveform shape of the beat is low are excluded as targets of calculation of the pulse wave analysis index.

8 Claims, 29 Drawing Sheets

(51) Int. Cl.
*A61B 5/00* (2006.01)
*A61B 5/053* (2006.01)

(56) References Cited

U.S. PATENT DOCUMENTS

2006/0224074 A1 10/2006 Ouchi et al.
2009/0018408 A1 1/2009 Ouchi et al.

FOREIGN PATENT DOCUMENTS

| JP | A-2004-136107 | 5/2004 |
| JP | A-2006-247221 | 9/2006 |
| JP | A-2006-271731 | 10/2006 |
| JP | A-2008-168073 | 7/2008 |
| JP | A-2009-11585 | 1/2009 |

\* cited by examiner

FIG. 7

| Beat No. i | Right upper arm | Left upper arm | Right ankle | Left ankle |
|---|---|---|---|---|
| 1 | 0 | 0 | 0 | 0 |
| 2 | 0 | 0 | 0 | 0 |
| 3 | 1 | 0 | 0 | 0 |
| 4 | 0 | 1 | 0 | 0 |
| 5 | 0 | 0 | 1 | 0 |
| 6 | 0 | 0 | 1 | 1 |
| 7 | 0 | 0 | 0 | 0 |
| ⋮ | ⋮ | ⋮ | ⋮ | ⋮ |
| n | 0 | 0 | 0 | 0 |

FIG. 28

| ID | Device | | Observer order |
|---|---|---|---|
| | Index | Order | |
| 1 | 70% | 14 | 14 |
| 2 | 93% | 3 | 2 |
| 3 | 94% | 2 | 3 |
| 4 | 89% | 5 | 4 |
| 5 | 89% | 6 | 1 |
| 6 | 75% | 13 | 11 |
| 7 | 81% | 12 | 9 |
| 8 | 57% | 17 | 15 |
| 9 | 94% | 1 | 5 |
| 10 | 85% | 7 | 7 |
| 11 | 82% | 10 | 17 |
| 12 | 83% | 8 | 12 |
| 13 | 81% | 11 | 10 |
| 14 | 82% | 9 | 8 |
| 15 | 90% | 4 | 6 |
| 16 | 65% | 16 | 16 |
| 17 | 68% | 15 | 13 |

# PULSE WAVE ANALYSIS DEVICE AND RECORDING MEDIUM

This is a Continuation of Application No. PCT/JP2010/069093 filed Oct. 27, 2010, which in turn is a PCT application, which claims the benefit of U.S. Japanese Patent Application No. 2009-250928 filed Oct. 30, 2009. The disclosure of the prior applications are hereby incorporated by reference herein in its entirety.

TECHNICAL FIELD

This disclosure relates to a pulse wave analysis device, and in particular to a pulse wave analyzing device and a recording medium having recorded thereon a pulse wave analysis program that can calculate a predetermined pulse wave analysis index by analyzing a pulse waveform for multiple beats.

BACKGROUND ART

Pulse wave analysis is used in the measurement of a pulse wave analysis index such as pulse wave velocity. Pulse wave velocity is utilized in medical practice as an index for non-invasively evaluating vein hardness.

The following are examples of techniques for precisely measuring a pulse wave analysis index.

JP 2006-247221A (Patent Literature 1) discloses that a determination as to whether a pulse wave includes noise is made using an autocorrelation function waveform.

JP 2001-128946A (Patent Literature 2) discloses the detection of notches and the calculation of a pulse wave velocity based on a time difference between such notches in order to measure accurate pulse wave velocity information.

JP H10-328150A (Patent Literature 3) discloses the calculation of a pulse wave velocity using the line with the largest slope and the base line of a heartbeat synchronized wave in order to highly precisely measure a pulse wave velocity.

JP 2008-168073A (Patent Literature 4) discloses the detection of a feature point of an acquired pulse wave and the display of a pulse waveform on a screen in real-time with the feature point being clearly indicated, in order to improve reliability and efficiency in arterial sclerosis evaluation.

SUMMARY OF INVENTION

Pulse wave velocity, which is one type of pulse wave analysis index, is obtained by a method such as the following. In the case of a brachial-ankle pulse wave velocity (baPWV), which is one form of pulse wave velocity, cuffs wrapped around the upper arm and the ankle are kept at a certain pressure, and the obtained pulse volume recording (PVR) waveform is recorded for several beats to a dozen or so beats. The pulse wave velocity is then calculated by detecting the pulse wave rising position of each beat in both the upper arm PVR waveform and the ankle PVR waveform.

With such a method, the pulse waves for all beats are used in the calculation of the pulse wave analysis index, and therefore if an arrhythmia, body movement, or the like occurs while obtaining the PVR waveform, a pulse wavecan become disrupted, and the index measurement precision degrades. As a result, there is the risk of an erroneous measurement value (low-precision pulse wave analysis index) being used in diagnosis.

The proposals made in the above patent literature therefore cannot be said to be sufficient for highly precisely calculating a pulse wave analysis index.

Aspects of this disclosure are directed to the above issues, and an object thereof is to provide a pulse wave analysis device and a recording medium having recorded thereon a pulse wave analysis program that can highly precisely calculate a pulse wave analysis index.

A pulse wave analysis device according to one aspect of the present invention includes: a storage unit for storing a pulse waveform for a plurality of beats; an analysis processing unit that performs processing for calculating a pulse wave analysis index by analyzing the pulse waveform for a plurality of beats; and an output unit for outputting the calculated pulse wave analysis index as an analysis result. The analysis processing unit integrates pulse waveform shapes of each beat that constitute the pulse waveform for a plurality of beats so as to obtain an integrated pulse waveform shape, and calculates the pulse wave analysis index after excluding, as a calculation target, a beat for which a degree of approximation between the integrated pulse waveform shape and the pulse waveform shape of the beat is low.

The analysis processing unit furthermore can calculate a degree of stability of beating by integrating the degrees of approximation of each pulse waveform shape used in calculation of the pulse wave analysis index, and the output unit furthermore outputs the degree of stability as an index indicating reliability of the pulse wave analysis index.

The storage unit can store the pulse waveform for a plurality of beats for each extremity, and, for each extremity, the analysis processing unit integrates the pulse waveform shapes of each beat and calculates the degree of approximation, the pulse wave analysis index, and the degree of stability, and the output unit outputs, as the analysis result, the pulse wave analysis index for which the degree of stability is the highest.

The storage unit can store the pulse waveform for a plurality of beats for a left extremity and a right extremity, and the analysis processing unit calculates the degree of approximation for each extremity, and calculates the pulse wave analysis index using the pulse waveform shape of the extremity for which the degree of approximation is the highest.

In calculating the degree of approximation, the analysis processing unit can limit the pulse waveform shapes of each beat to a range having influence on calculation of the pulse wave analysis index.

The pulse wave analysis index may indicate a degree of arterial sclerosis and/or a degree of blood vessel stenosis.

The pulse wave analysis index can include a pulse wave velocity as an index indicating the degree of arterial sclerosis.

The pulse wave analysis device can further include a pulse wave detection unit for detecting a pulse wave of an extremity, wherein the analysis processing unit calculates the pulse waveform for a plurality of beats based on a detection signal from the pulse wave detection unit.

A recording medium according to another aspect of the present invention has recorded thereon a pulse wave analysis program for causing a computer to function as a device for analyzing a pulse wave. The pulse wave analysis program causes the computer to execute the steps of: integrating pulse waveform shapes of each beat that constitute a pulse waveform for a plurality of beats stored in a storage unit so as to obtain an integrated pulse waveform shape; calculating a pulse wave analysis index after excluding, as a calculation target, a beat for which a degree of approximation between the integrated pulse waveform shape and the pulse waveform shape of the beat is low; and outputting the calculated pulse wave analysis index as an analysis result.

One aspect of the invention is to enable calculating a pulse wave analysis index using only stable beats including little influence from body movement and the like. As a result, a highly precise pulse wave analysis index can be output as an analysis result.

BRIEF DESCRIPTION OF DRAWINGS

FIG. 7 is a diagram showing an example of exclusion processing results in step S108 of FIG. 6.

FIG. 28 is a diagram showing the relationship between the order of degrees of approximation calculated by a device and the order of degrees of approximation made by an observer in the case of targeting the pulse waveforms of FIGS. 11A to 27B.

DETAILED DESCRIPTION OF EMBODIMENTS

Figure 1:
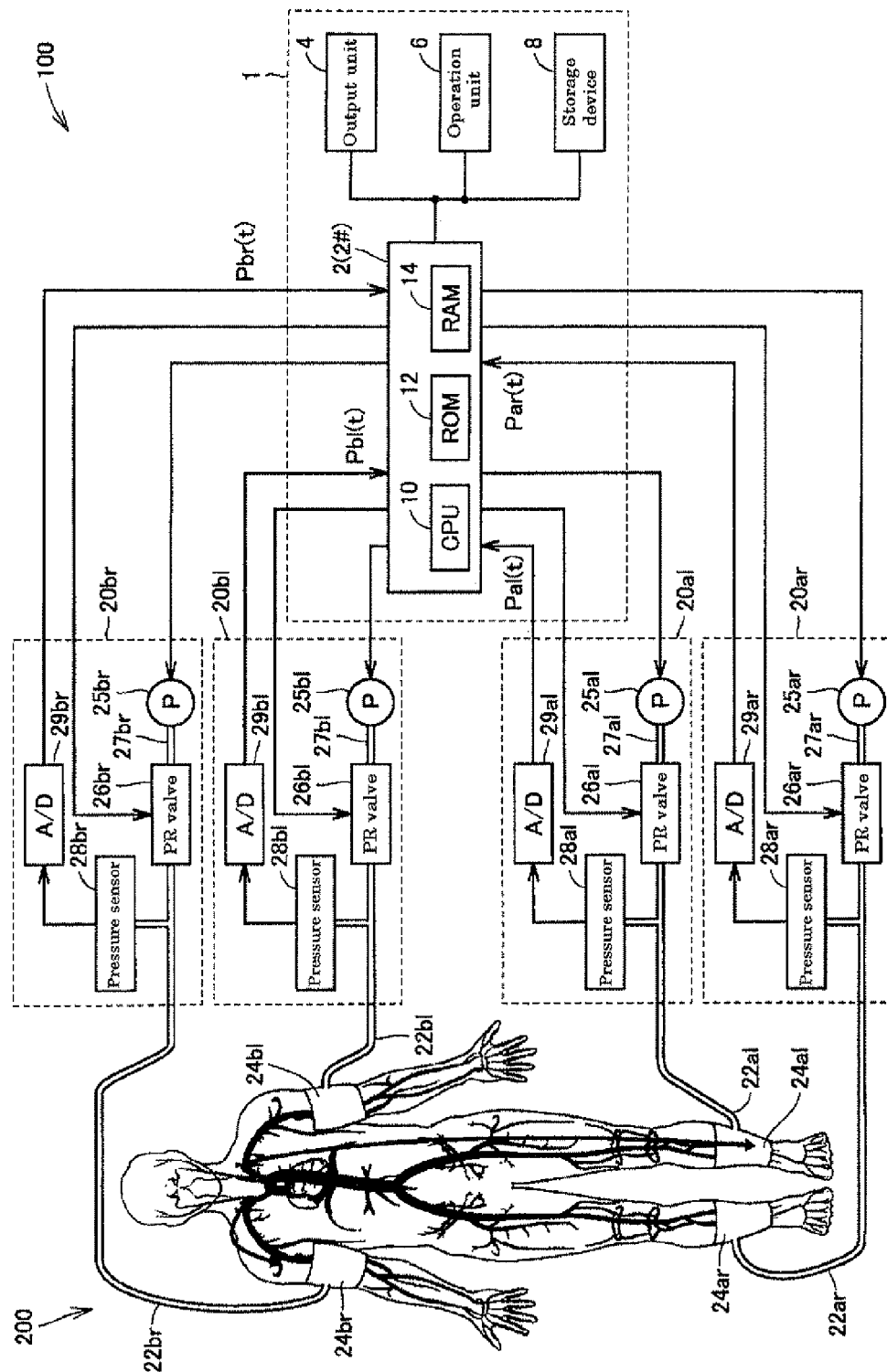
FIG. 1 is a schematic configuration diagram of a pulse wave analysis device according to an embodiment of the present invention.

The following is a detailed description of embodiments of the present invention with reference to the drawings. Note that the same reference signs have been given to corresponding portions in the drawings, and redundant descriptions thereof will not be given.

Schematic Configuration

FIG. 1 is a schematic configuration diagram of a pulse wave analysis device 100 according to an embodiment of the present invention.

As shown in FIG. 1, the pulse wave analysis device 100 includes an information processing unit 1, four detection units 20ar, 20al, 20br, and 20bl, and four cuffs 24ar, 24al, 24br, and 24bl.

The cuffs 24ar, 24al, 24br, and 24bl are worn on respective extremities of a measurement subject 200. Specifically, they are respectively worn on the right upper arm (upper right limb), left upper arm (upper left limb), right ankle (lower right limb), and left ankle (lower left limb). Note that "extremity" refers to a site on any of the four limbs, and may be a wrist, a finger, or the like. The cuffs 24ar, 24al, 24br, and 24bl will be collectively referred as "cuffs 24" when there is no particular need to distinguish between them.

The detection units 20ar, 20al, 20br, and 20bl each include hardware necessary for detecting a pulse wave of an extremity of the measurement subject 200. Since it is sufficient that the detection units 20ar, 20al, 20br, and 20bl all have a similar configuration, they will be collectively referred to as "detection units 20" when there is no particular need to distinguish between them.

The information processing unit 1 includes a control unit 2, an output unit 4, an operation unit 6, and a storage device 8.

The control unit 2 is a device that performs overall control of the pulse wave analysis device 100, and is typically configured by a computer including a CPU (Central Processing Unit) 10, a ROM (Read Only Memory) 12, and a RAM (Random Access Memory) 14.

The CPU 10 corresponds to an arithmetic processing unit, and the CPU 10 reads out a program stored in the ROM 12 in advance, and executes the program while using the RAM 14 as a work memory.

Also, the control unit 2 is connected to the output unit 4, the operation unit 6, and the storage device 8. The output unit 4 outputs measured pulse waves, pulse wave analysis results, and the like. The output unit 4 may be a display device configured by an LED (Light Emitting Diode) display, an LCD (Liquid Crystal Display) or the like, or a printer (driver).

The operation unit 6 receives instructions from a user. The storage device 8 holds various types of data and programs. The CPU 10 of the control unit 2 reads out data and programs recorded in the storage device 8, as well as performs writing to the storage device 8. The storage device 8 may be configured by, for example, a hard disk, a nonvolatile memory (e.g., a flash memory), or a detachable external recording medium.

The following is a specific description of the configuration of the detection units 20.

The detection unit 20br detects a pulse wave in the right upper arm by adjusting and detecting the internal pressure of the cuff 24br (hereinafter, referred to as "cuff pressure") worn on the right upper arm of the measurement subject 200. The cuff 24br contains a fluid bag (e.g., an air bag) that is not shown.

The detection unit 20br includes a pressure sensor 28br, a pressure regulation salve (abbreviated as "PR valve" in FIG. 1) 26br, a pressure pump 25br, an A/D (Analog to Digital) conversion unit 29br, and a tube 27br. The cuff 24br is connected to the pressure sensor 28br and the pressure regulation valve 26br by the tube 22br.

The pressure sensor 28br includes multiple sensor elements arranged with a predetermined interval on a semiconductor chip made of monocrystalline silicon or the like at a detection site for detecting pressure fluctuation transmitted via the tube 22br. The pressure fluctuation signal detected by the pressure sensor 28br is converted into a digital signal by the A/D conversion unit 29br, and the digital signal is input to the control unit 2 as a pulse wave signal Pbr(t).

The pressure regulation valve 26br is inserted between the pressure pump 25br and the cuff 24br, and maintains the pressure used in pressurization of the cuff 24br so as to be in a predetermined range during measurement. The pressure pump 25br operates in accordance with a detection instruction from the control unit 2, and supplies air to the fluid bag (not shown) in the cuff 24br in order to pressurize the cuff 24br.

Due to this pressurization, the cuff 24br is pressed against a measurement site, and pressure variations according to a pulse wave of the right upper arm are transmitted to the detection unit 20br via the tube 22br. The detection unit 20br detects the pulse wave of the right upper arm by detecting the transmitted pressure variations.

Similarly, the detection unit 20bl also includes a pressure sensor 28bl, a pressure regulation valve 26bl, a pressure pump 25bl, an A/D conversion unit 29bl, and a tube 27bl. The cuff 24bl is connected to the pressure sensor 28bl and the pressure regulation valve 26bl by the tube 22bl.

Also, the detection unit 20ar includes a pressure sensor 28ar, a pressure regulation valve 26ar, a pressure pump 25ar, an A/D conversion unit 29ar, and a tube 27ar. The cuff 24ar is connected to the pressure sensor 28ar and the pressure regulation valve 26ar by the tube 22ar.

Similarly, the detection unit 20al also includes a pressure sensor 28al, a pressure regulation valve 26al, a pressure pump 25al, an A/D conversion unit 29al, and a tube 27al. The cuff 24al is connected to the pressure sensor 28al and the pressure regulation valve 26al by the tube 22al.

The functions of the portions in the detection units 20bl, 20ar, and 20al are similar to those of the detection unit 20br, and therefore redundant detailed descriptions will not be given. Also, the signs "ar", "br", and the like will be omitted from the description of the portions in the detection units 20 when there is no particular need to distinguish between them.

Note that although a configuration for detecting a pulse wave using the pressure sensor 28 is described in the present embodiment, it is possible to use a configuration for detecting a pulse wave using an artery volume sensor (not shown). In this case, the artery volume sensor may include, for example, a light emitting element for irradiating an artery with light, and a light receiving element for receiving the light irradiated by the light emitting element as light that has passed through the artery or been reflected thereby. Alternatively, a configuration is possible in which multiple electrodes are provided for applying a minute constant current to a measurement site of the measurement subject 200 and detecting voltage variations that occur due to variations in impedance (biological impedance) occurring in accordance with pulse wave propagation.

Figure 2:
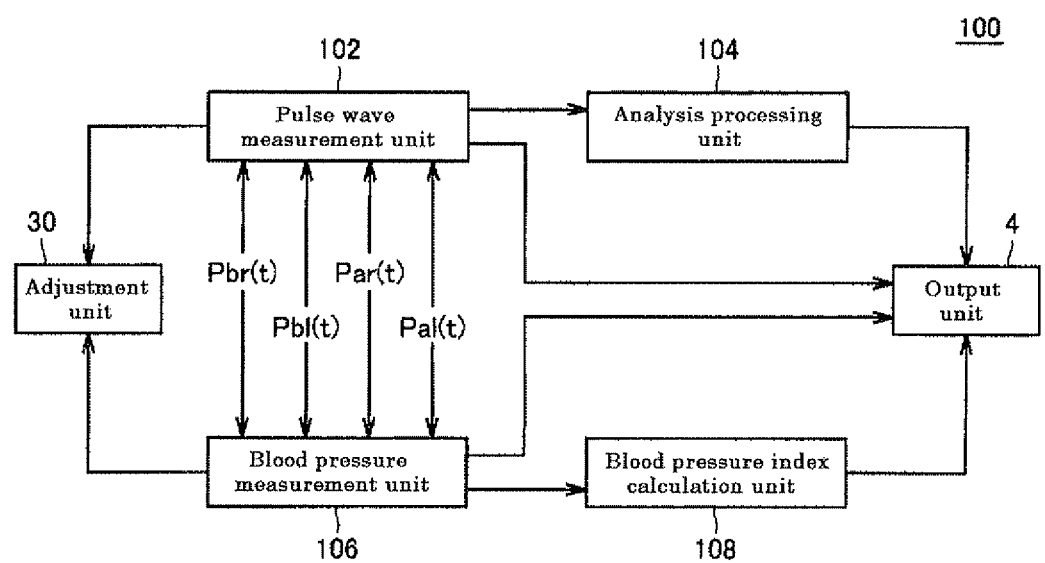
FIG. 2 is a functional block diagram showing a functional configuration of the pulse wave analysis device according to an embodiment of the present invention.

FIG. 2 is a block diagram showing a configuration of the pulse wave analysis device 100.

As shown in FIG. 2, the pulse wave analysis device 100 of the present embodiment includes, as functions, an adjustment unit 30, a pulse wave measurement unit 102, an analysis processing unit 104, a blood pressure measurement unit 106, a blood pressure index calculation unit 108, and an output unit 4. In some embodiments, the blood pressure measurement unit 106 and the blood pressure index calculation unit 108 may not be included in the functional configuration of the pulse wave analysis device 100.

The adjustment unit 30 is a functional unit that adjusts the pressure inside the cuffs 24. The functionality of the adjustment unit 30 is achieved by the pressure pumps 25 and the pressure regulation valves 26 shown in FIG. 1, for example.

The pulse wave measurement unit 102 is connected to the adjustment unit 30 and the A/D conversion unit 29, and performs processing for measuring a pulse wave (PVR) in each extremity. The pulse wave measurement unit 102 adjusts the internal pressure of the cuffs 24 by transmitting an instruction signal to the adjustment unit 30, and receives cuff pressure signals Par(t), Pal(t), Pbr(t), and Pbl(t) that were detected in response to the instruction signal. The received cuff pressure signals Par(t), Pal(t), Pbr(t), and Pbl(t) are then recorded in time series, thus acquiring a pulse waveform for multiple beats for each extremity. Pulse wave measurement is performed for a predetermined time (e.g., approximately 10 sec), for example.

The pulse wave measurement results obtained by the pulse wave measurement unit 102 may be output to the output unit 4.

Figure 3:
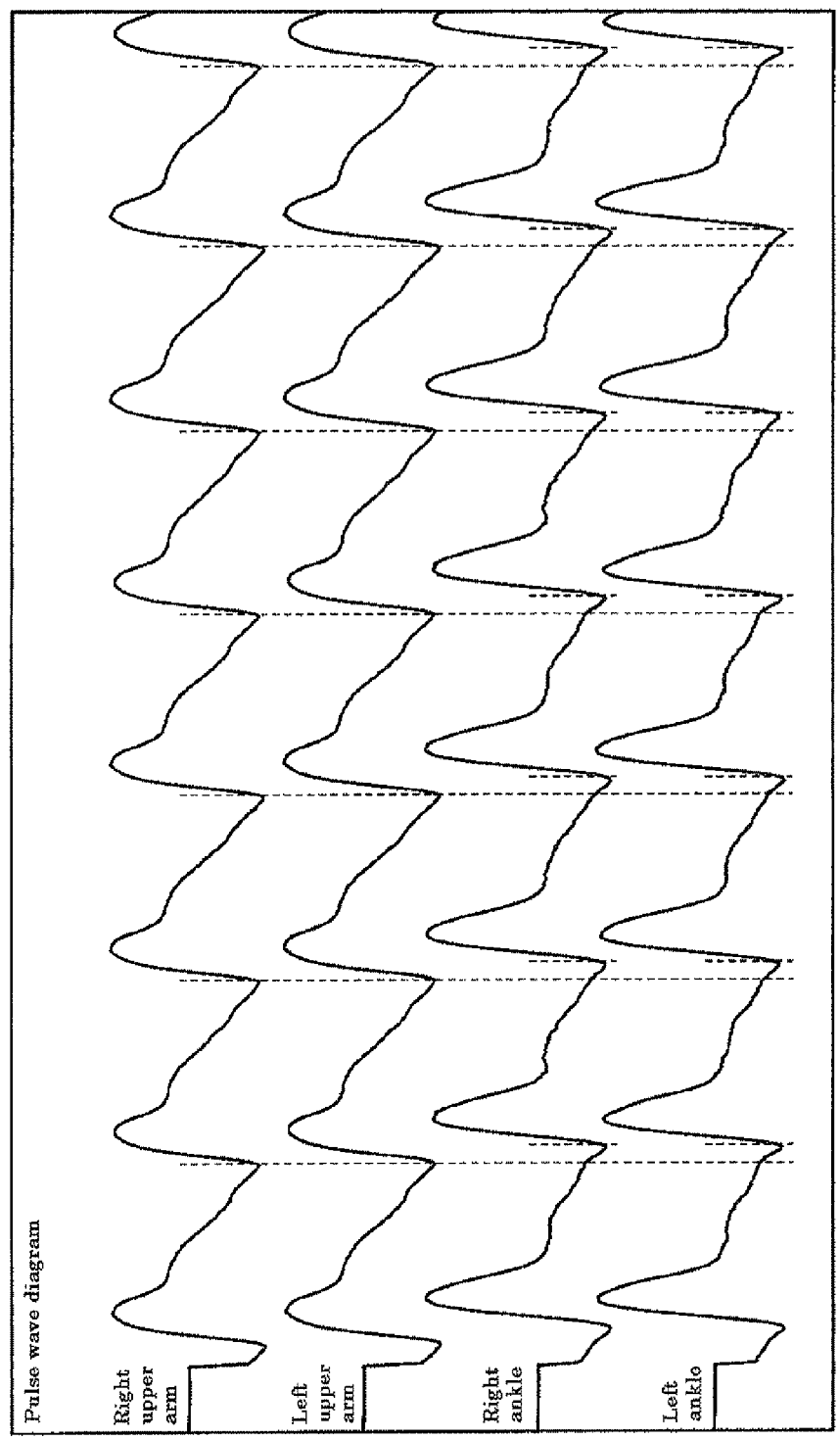
FIG. 3 is a diagram showing an example of pulse wave measurement results for each extremity.

FIG. 3 is a diagram showing an example of pulse wave measurement results for each extremity. In FIG. 3, the pulse waveforms of the extremities are shown along the same time axis. The rising position of the pulse waves of each beat may be indicated by a broken line or the like, as shown in FIG. 3.

The analysis processing unit 104 analyzes the pulse waves of each extremity measured by the pulse wave measurement unit 102 so as to calculate a predetermined pulse wave analysis index (hereinafter, abbreviated as an "analysis index") as a feature quantity of pulse waves of the measurement subject 200 (FIG. 1). In the present embodiment, the "analysis index" refers to an index having a correlation with arterial sclerosis and/or blood vessel stenosis. In other words, the "analysis index" indicates the degree of arterial sclerosis and/or the degree of blood vessel stenosis.

Examples of an analysis index indicating the degree of arterial sclerosis include pulse wave velocity, PTT (Pulse Transit Time), AI (Augmentation Index), and TR (Traveling time to Reflected wave). Note that the pulse wave velocity is not limited to being calculated using upper arm pulse waves and ankle pulse waves (i.e., a baPWV), and it is possible for the pulse wave velocity to be calculated using pulse waves of two other measurement sites or only the pulse wave of one measurement site (extremity).

Examples of an analysis index indicating the degree of blood vessel stenosis include a rising feature value of an ankle pulse wave and a pulse wave sharpness. The rising feature value of an ankle pulse wave is calculated as a UT (Upstroke Time), for example. The UT is calculated as the rising period of the ankle pulse wave from the rising point to the peak. The pulse wave sharpness is calculated as a % MAP (normalized pulse wave area). Here, % MAP is calculated as, for example, the percentage of M with respect to H (=M/H×100), where M is the height from the lowest blood pressure when the pulse wave area is equalized, and H is the peak height of the pulse wave (i.e., pulse pressure).

Although the baPWV is calculated as the analysis index in the description of the present embodiment, other feature quantities such as those described above may be calculated.

The analysis processing unit 104 performs processing for recognizing the pulse waveform shape (shape of the pulse waveform) of each beat in a pulse waveform for multiple beats. Specifically, the analysis processing unit 104 performs pulse wave separation processing so as to extract a pulse waveform for each beat. Accordingly, a pulse waveform shape is recognized for each beat. This pulse wave separation processing can be realized by a known technique such as differential processing or filter processing using a specific frequency.

The analysis processing unit 104 integrates the recognized pulse waveform shapes of each beat, and calculates a degree of approximation between the integrated pulse waveform shape (hereinafter, also referred to as the "integrated shape") and each beat. Although "integrates the recognized pulse waveform shapes of each beat" refers to averaging the pulse waveform shapes of each beat in the present embodiment, it is possible to perform processing equivalent to averaging.

In the present embodiment, a "degree of approximation" is a value indicating the degree to which two waveforms approximate each other, and more specifically "degree of approximation" refers to a numerical value indicating the extent to which two waveforms match. The degree of approximation is obtained using Expression (1) shown below, for example.

$$\text{DEGREE OF APPROXIMATION} = \frac{1}{\sum |(Pi - Pa)|} \quad (1)$$

Figure 4:
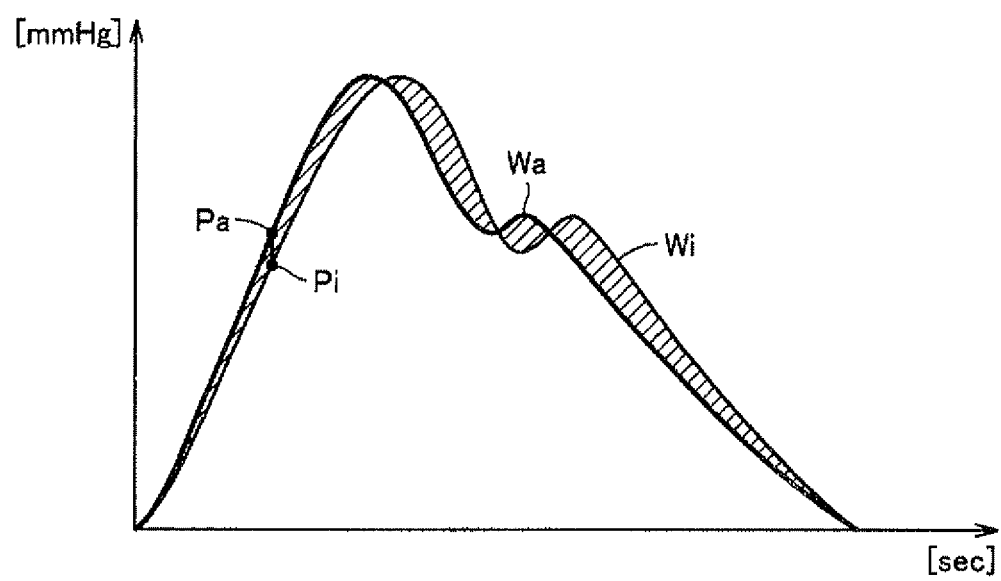
FIG. 4 is a diagram for illustrating a method of calculating the degree of approximation between an integrated pulse waveform shape and each beat according to an embodiment of the present invention.

FIG. 4 is a diagram for illustrating a method of calculating the degree of approximation between an integrated shape and each beat according to one embodiment of the present invention.

As shown in FIG. 4, the degree of approximation is calculated as the inverse of the area produced by misalignment between an integrated shape Wa and a measured pulse waveform shape Wi of the i-th beat. In other words, the degree of approximation can be obtained as the inverse of the sum value of the difference between amplitude values Pa and Pi in each sampling time when the pulse rise is used as the origin.

Also, the degree of approximation may be obtained as the inverse of the integral value of the difference between the amplitude values Pa and Pi in each sampling time.

Also, it is possible to weight the difference between the amplitude values Pa and Pi, and obtain the degree of approximation using the inverse of the square sum of the differences between the amplitude values Pa and Pi as shown in Expression (2) shown below.

$$\text{DEGREE OF APPROXIMATION} = \frac{1}{\sum (Pi - Pa)^2} \quad (2)$$

The expression for calculating the degree of approximation is determined based on the results of experimentation performed in advance. A method (principle) for setting the degree of approximation calculation expression will be described later.

Note that although the degree of approximation with an integrated pulse wave is obtained for the pulse waves of all of the beats using the pulse rise as the origin in the present embodiment, the section used in the calculation of the degrees of approximation may be limited to a range that greatly influences the analysis index. For example, the section may be limited to the range from the rising point of the pulse waveform to the peak, or may be limited to the former half of the pulse waveform. In other words, a configuration is possible in which the latter half of the pulse waveform shape of one beat, which does not influence the calculation of the analysis index, is not used in the calculation of the degree of approximation.

Also, although the difference between amplitude values when the pulse rise is the origin is used in the calculation of the degree of approximation, the position of the origin (the position at which two waveforms are matched) is not limited to the pulse rise. For example, the origin point may be determined to be a certain reference position such as the peak of the pulse waveform. Alternatively, instead of a certain reference point, the origin may be determined to be the position of each beat at which the degree of approximation with the integrated waveform is the highest.

Also, although a degree of approximation is calculated in the present embodiment, a "degree of misalignment" with the integrated shape may be calculated. The degree of misalignment can be calculated as the inverse of the degree of approximation obtained using Expression (1) or (2).

The analysis processing unit 104 specifies beats for which the pulse waveform shape was determined to have a low degree of approximation (i.e., high degree of misalignment) with the integrated shape, and excludes the specified beats as targets of the calculation of the analysis index. Excluding pulse waveform shapes whose degree of approximation with the integrated shape is low in this way appropriately excludes pulse waves that are unstable and have a high possibility of having been sporadically disrupted due to an arrhythmia or body movement.

Conventionally, when pulse waveforms for multiple beats as shown in FIG. 3 have been measured, a physician has visually determined whether the waveforms have been disrupted, but according to the present invention, a degree of approximation with an integrated shape is calculated, thus enabling determining whether a waveform is disrupted based on an arithmetic operation.

The analysis processing unit 104 calculates the baPWV by analyzing only the pulse waveforms of beats that have not been excluded, that is to say, only stable pulse waveforms. In the present embodiment, the analysis processing unit 104 calculates two types of baPWV using both the left and right ankles as measurement sites, such as an right upper arm-left ankle pulse wave velocity (hereinafter, also referred to as the "baPWV_RL") and an right upper arm-right ankle pulse wave velocity (hereinafter, also referred to as the "baPWV_RR"). Two types of baPWV are calculated in this way because the difference therebetween can also be used in the diagnosis of arterial stenosis in the left lower leg and right lower leg.

Note that although the upper arm measurement site is on the right side in the present embodiment because this has been determined as a default, the left side may be used as a reference. Also, for example, in the case where the blood pressure in the right upper arm is lower than the blood pressure of the left upper arm by a predetermined value (e.g., 16 mmHg to 20 mmHg) or more, the left upper arm may be used as the measurement site instead of the right upper arm. Also, a configuration is possible in which the left upper arm is used as the measurement site instead of the right upper arm in the case where an instruction to use a measurement site on the left side has been input via the operation unit 6.

When calculating the baPWV_RL and the baPWV_RR, only the pulse waveforms of beats that have not been excluded are used in analysis. The analysis processing unit 104 calculates, for each targeted beat, a time difference (times Tr and Tl in FIG. 5) between the rising positions of the upper arm pulse wave and the ankle pulse wave, and calculates the two types of baPWV by dividing the average value of the calculated times by the length of the blood vessel (i.e., the pulse wave transit distance).

Figure 5:
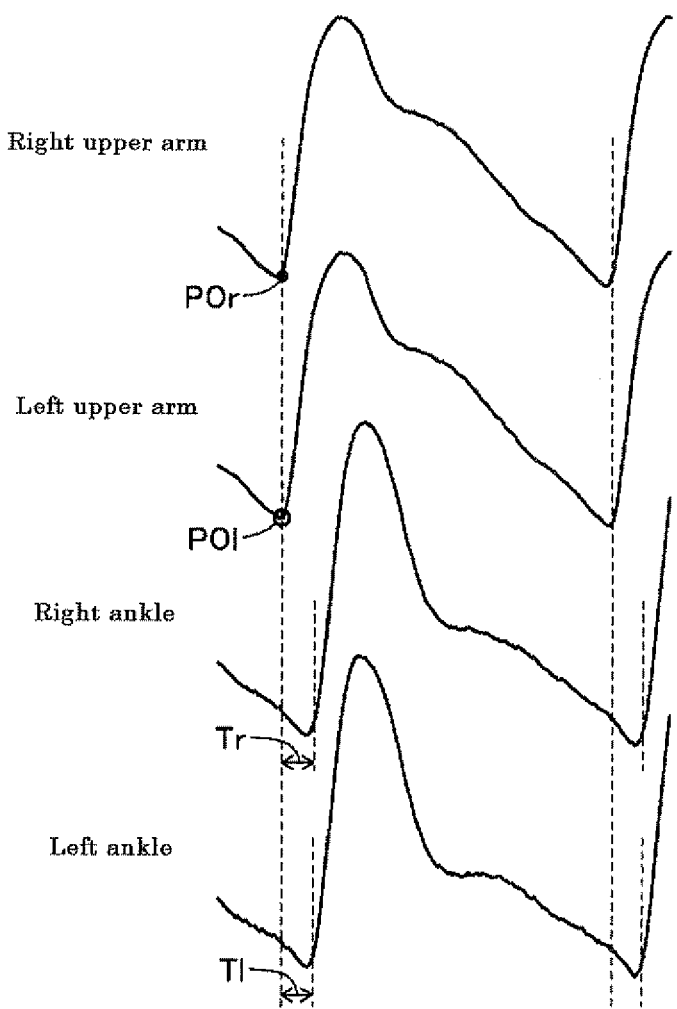
FIG. 5 is a diagram for illustrating a method of calculating a pulse wave transit distance.

In FIG. 5, the times Tr and Tl indicate time differences from a rising point P0r of the right upper arm pulse wave. In the case of using the left upper arm as the measurement site, time differences from a rising point P0l of the left upper arm pulse wave are used to calculate a left upper arm-left ankle pulse wave velocity (hereinafter, also referred to as the "baPWV_LL") and a left upper arm-right ankle pulse wave velocity (hereinafter, also referred to as "baPWV_LR"). The times Tr and Tl in FIG. 5 indicate pulse transit times (PTTs).

Note that the blood vessel length, which is necessary in the calculation of the two types of baPWV, is calculated by applying the height of the measurement subject to a predetermined conversion expression. The height of the measurement subject is input using the operation unit 6, for example.

The analysis processing unit 104 may furthermore calculate a degree of stability of beating for all of the pulse waves used in the calculation of the analysis index, by integrating the degrees of approximation of the pulse waveform shapes used in the calculation of the analysis index. In the present embodiment, a degree of stability of beating for all of the pulse waves targeted for calculation is calculated for each of baPWV_RL and baPWV_RR. The degree of stability of beating is derived based on the pulse waveforms used in baPWV calculation instead of the pulse waveforms of all of the beats that were measured, and therefore the degree of stability of beating has a direct relationship with the reliability of the baPWV. Accordingly, it can be said that degrees of stability of beating calculated by the analysis processing unit 104 indicate the reliability (degree to which the value is reliable) of the corresponding baPWV.

Note that in the case where a degree of misalignment is calculated instead of a degree of approximation, a value obtained by integrating the degrees of misalignment of the pulse waveform shapes used in the calculation of the analysis index is calculated as degree of disruption of beating for all of the pulse waves used in the calculation of the analysis index.

The two types of baPWV and the degrees of stability calculated by the analysis processing unit 104 are output to the output unit 4. The output unit 4 outputs the baPWV_RL and the baPWV_RR, and also outputs indices respectively indicating the reliability of the two types of baPWV, in association with the corresponding baPWV. The values calculated as the degrees of stability of beating may be output as the indices indicating the reliability of the two types of baPWV, or level values, marks, signs, or the like may be substituted for the calculated values and output as the indices indicating the reliability of the two types of baPWV.

Similarly to the pulse wave measurement unit 102, the blood pressure measurement unit 106 is connected to the adjustment unit 30 and the A/D conversion unit 29, and performs processing for measuring the blood pressure at each extremity. The blood pressure measurement unit 106 adjusts the internal pressure of the cuffs 24 by transmitting an instruction signal to the adjustment unit 30, and receives cuff pressure signals Par(t), Pal(t), Pbr(t), and Pbl(t) that were detected in response to the instruction signal. The blood pressure measurement unit 106 measures a systolic blood pressure and a diastolic blood pressure for each extremity of the measurement subject 200 in accordance with a known oscillometric technique. More specifically, the systolic blood pressure and the diastolic blood pressure are calculated for each extremity by quickly raising the cuff pressure to a predetermined pressure value and then applying time-series cuff pressure signals detected while gradually reducing the pressure to a predetermined algorithm. The blood pressure measurement unit 106 may furthermore measure the number of pulse beats, average blood pressure, and pulse pressure.

The blood pressure index calculation unit 108 calculates a predetermined blood pressure index based on the blood pressure values measured by the blood pressure measurement unit 106. The "blood pressure index" of the present embodiment refers to an index having a correlation with the degree of blood vessel clogging (degree of arterial stenosis), and one specific example thereof is the ABI (Ankle Brachial Index). In the present embodiment, the ABI is calculated using both the left and right ankles and either upper arm as measurement sites. For example, the ratio of the right upper arm systolic blood pressure and the right ankle systolic blood pressure and the ratio of the right upper arm systolic blood pressure and the left ankle systolic blood pressure are respectively calculated as "ABI_RR" and "ABI_RL". Note that in the calculation of each ABI as well, the right upper arm may be used as the measurement site in the case where the right upper arm systolic blood pressure is higher than that of the left upper arm, and the left upper arm may be used as the measurement site in the case where the left upper arm systolic blood pressure is higher than that of the right upper arm. Also, the average of the right upper arm and left upper arm systolic blood pressures may be used as the upper arm blood pressure in ABI calculation. Also, although an ABI is calculated as the blood pressure index in the present embodiment, another blood pressure feature quantity may be used.

The measurement results of the blood pressure measurement unit 106 and the ABI_RR and the ABI_RL calculated by the blood pressure index calculation unit 108 are output to the output unit 4. The output unit 4 outputs the baPWV_RL, the baPWV_RR, and the indices respectively indicating the reliability thereof, along with the blood pressure values of each extremity, and the ABI_RR and ABI_RL. Accordingly, a healthcare professional such as a physician can more accurately diagnose whether there is the suspicion of arterial sclerosis.

The operations of the pulse wave measurement unit 102, the analysis processing unit 104, the blood pressure measurement unit 106, and the blood pressure index calculation unit 108 described above may be realized by executing software stored in the ROM 12, or the operations of at least one of the above units may be realized by hardware. Also, a portion of the processing executed by the analysis processing unit 104 may be realized by hardware.

Operations

Next is a description of operations performed by the pulse wave analysis device 100 of the present embodiment. The following description of operations focuses on processing executed by the analysis processing unit 104.

Figure 6:
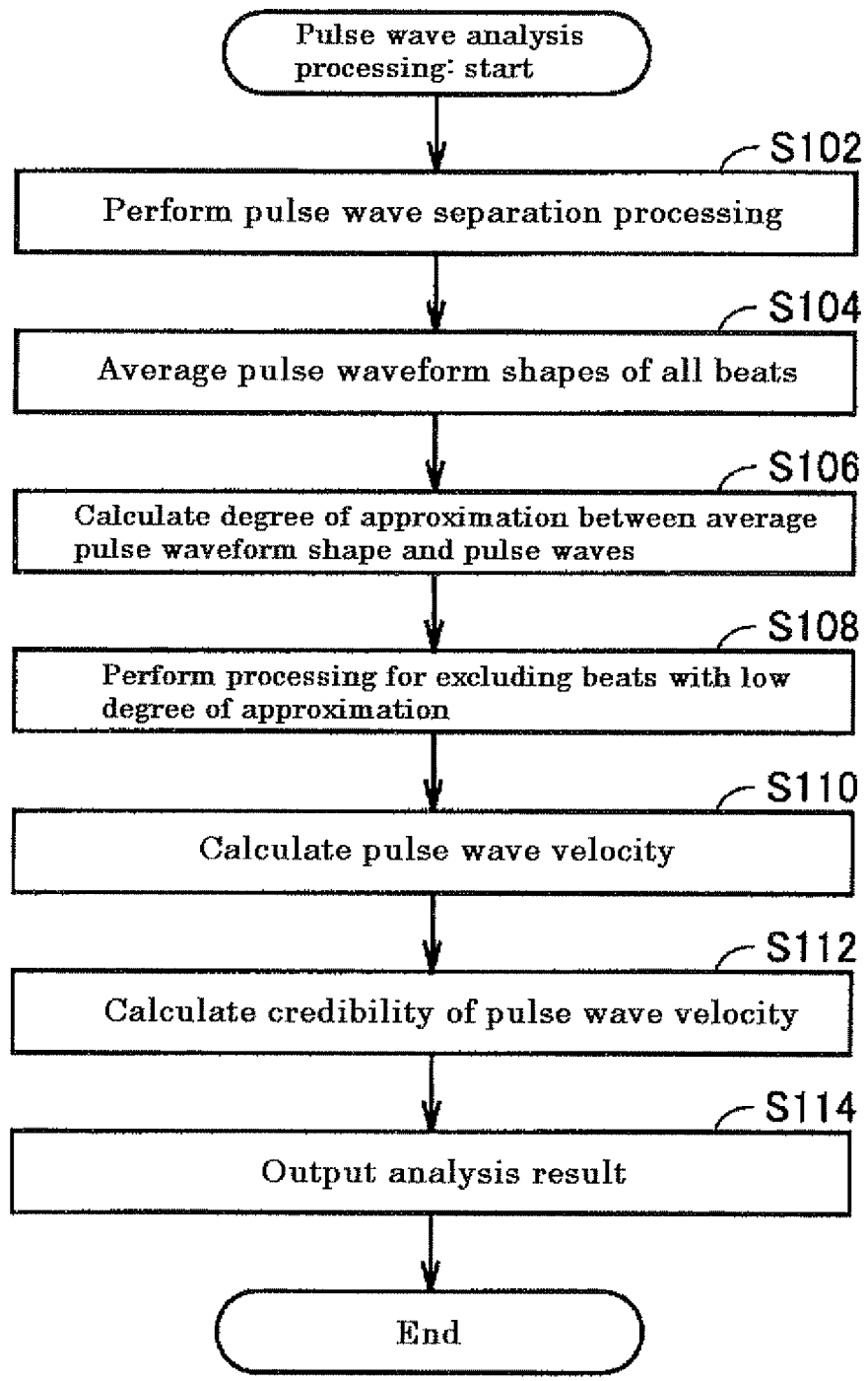
FIG. 6 is a flowchart showing pulse wave analysis processing according to an embodiment of the present invention.

FIG. 6 is a flowchart showing pulse wave analysis processing according to the embodiment of the present invention. The processing shown in the flowchart of FIG. 6 is stored in advance as a program in the ROM 12, and the functionality of the pulse wave analysis processing is realized by the CPU 10 reading out and executing the program.

Note that it is assumed that when the pulse wave analysis processing is started, pulse waveforms for each extremity that have been measured by the pulse wave measurement unit 102 are stored in the RAM 14 or the storage device 8. In other words, the pulse wave analysis processing of the present embodiment is not limited to being performed immediately after pulse wave measurement, and may be performed on pulse waveforms measured in the past that are stored in the storage device 8.

As shown in FIG. 6, for each extremity serving as a measurement site, the analysis processing unit 104 performs processing for separating the stored pulse waveform for multiple beats (step S102). Accordingly, the pulse waveform for multiple beats is separated beat-by-beat, and the pulse waveform shapes of each beat are recognized.

Subsequently, for each extremity, the analysis processing unit 104 averages the pulse waveform shapes of all of the beats that were recognized (step S104), and calculates a degree of approximation between the averaged pulse waveform shape (integrated shape) and each pulse waveform shape (step S106). For example, the above-described Expression (1) is used in the degree of approximation calculation. The degrees of approximation of each pulse wave calculated for each extremity are temporarily recorded in the RAM 14.

The analysis processing unit 104 performs processing for excluding beats for which the degree of approximation is low (step S108). Specifically, firstly, for each extremity, a pulse waveform shape for which the degree of approximation does not satisfy a certain condition (e.g., the degree of approximation is less than or equal to a predetermined threshold value) is specified, and the specified pulse waveform shape is excluded as a target of baPWV calculation. Note that the threshold value used in specifying such pulse waveform shapes is not limited to being a predetermined value. For example, a configuration is possible in which the threshold value is determined based on the average degree of approximation for all of the beats, and a pulse waveform shape that does not satisfy a condition using that reference (determined threshold value) is specified for exclusion as a target. As a result of the exclusion processing, information indicating whether pulse waveform shapes are to be used in baPWV calculation is temporarily recorded in the RAM 14.

FIG. 7 is a diagram showing an example of exclusion processing results in step S108 of FIG. 6.

As shown in FIG. 7, the information that is recorded indicates, in association with each beat i (i=1, 2, 3, ..., n), whether the pulse waveform shapes of the right upper arm, left upper arm, right ankle, and left ankle have been excluded as calculation targets. For example, in the present embodiment, "1" is recorded in a field corresponding to a Beat No. if it has been determined that the pulse waveform is to be excluded, and otherwise "0" is recorded. Note that the method of holding exclusion processing results for each extremity is not limited to the example shown in FIG. 7.

When the exclusion processing ends, baPWV (pulse wave velocity) calculation is performed in accordance with the processing results (step S110). In the present embodiment, as a result of the exclusion processing of step S108, beats determined as having a low degree of approximation are excluded, and both baPWV_RL and baPWV_RR are calculated.

The following describes the method of calculating each baPWV assuming that the results shown in FIG. 7 have been recorded. In the case of calculating the baPWV_RL, the right upper arm pulse wave and the left ankle pulse wave are used. As shown in FIG. 7, it has been recorded that the pulse wave of the 3rd beat of the right upper arm and the pulse wave of the 6th beat of the left ankle have been excluded as targets. Accordingly, the pulse waves of the 3rd beat and the 6th beat are excluded when calculating the baPWV_RL. More specifically, for each of the beats other than the 3rd beat and the 6th beat, the pulse transit times of the pulse waves of the right upper arm and the left ankle are calculated, and the baPWV_RL is calculated using the average value of the calculated pulse transit times and an estimated value of the blood vessel length.

In the case of calculating the baPWV_RR, the right upper arm pulse wave and the right ankle pulse wave are used. As shown in FIG. 7, it has been recorded that the pulse wave of the 3rd beat of the right upper arm and the pulse waves of the 5th and 6th beats of the right ankle have been excluded as targets. Accordingly, the pulse waves of the 3rd beat, the 5th beat, and the 6th beat are excluded when calculating the baPWV_RR. More specifically, for each of the beats other than the 3rd beat, the 5th beat, and the 6th beat, the pulse transit times of the pulse waves of the right upper arm and the right ankle are calculated, and the baPWV_RR is calculated using the average value of the calculated pulse transit times and an estimated value of the blood vessel length.

In this way, according to the present embodiment, a greatly disrupted pulse waveform is not used in the calculation of each baPWV, thus enabling reliably calculating an analysis index. Also, a pulse waveform shape to serve as a reference in degree of approximation calculation is obtained by integrating measured waveforms. This enables specifying pulse waveform shapes that are to be appropriately excluded in accordance with the clinical state or clinical condition of the measurement subject when measurement is performed, or a measurement condition (e.g., immediately after administration of medication).

Next, the analysis processing unit 104 calculates the reliability of each baPWV (step S112). In the present embodiment, a degree of stability of beating for all of the pulse waves used in calculation is calculated for each of baPWV_RL and baPWV_RR. Specifically, the degree of stability of beating for all of the pulse waves used in the calculation of the baPWV_RL (i.e., the reliability of the baPWV_RL) is calculated by integrating (e.g., averaging) the degrees of approximation of the beats used in the calculation of the baPWV_RL. Since the pulse waves of the 3rd beat and the 6th beat are excluded in the example in FIG. 7 in the calculation of the baPWV_RL, the reliability of the baPWV_RL is represented as a value obtained by averaging the degrees of approximation for the right upper arm and left ankle beats other than the 3rd beat and the 6th beat.

More specifically, among the right upper arm pulse waveform shapes, an average value is obtained for the degrees of approximation of the beats other than the 3rd beat and the 6th beat, and among the left ankle pulse waveform shapes, an average value is obtained for the degrees of approximation of the beats other than the 3rd beat and the 6th beat. A value obtained by then averaging these average values is calculated as a degree of stability for all of the pulse waves used in calculation.

Alternatively, a configuration is possible in which a value obtained by averaging the degrees of approximation of all of the beats other than the 3rd beat and the 6th beat among the right upper arm pulse waveform shapes and the degrees of approximation of all of the beats other than the 3rd beat and the 6th beat among the left ankle pulse waveform shapes is calculated as the degree of stability of all of the pulse waves used in calculation.

The reliability of the baPWV_RR is calculated using a similar method. Since the pulse waves of the 3rd beat, the 5th beat, and the 6th beat are excluded in the example in FIG. 7 in the calculation of the baPWV_RR, the reliability of the baPWV_RR is calculated by integrating (e.g., averaging) the degrees of approximation with the integrated shape for the beats other than the 3rd beat, the 5th beat, and the 6th beat.

In this way, the reliability of each type of baPWV is obtained by individually evaluating the degrees of approximation with the integrated shape, and thereafter integrating the degrees of approximation for all of the beats that were used in index calculation. Accordingly, the degree of influence of one beat on the whole can be made equivalent to that when using a conventionally performed baPWV calculation method (calculating a pulse transit time for each beat, and dividing an estimated value of the blood vessel length by the average of the pulse transit times).

When the above-described analysis processing ends, the analysis results are output to the output unit 4 (step S114). In the present embodiment, the output unit 4, which functions as a printer (driver), prints the obtained analysis results onto a paper medium. For example, the analysis result information shown in FIG. 8 is printed onto a paper medium.

Figure 8:
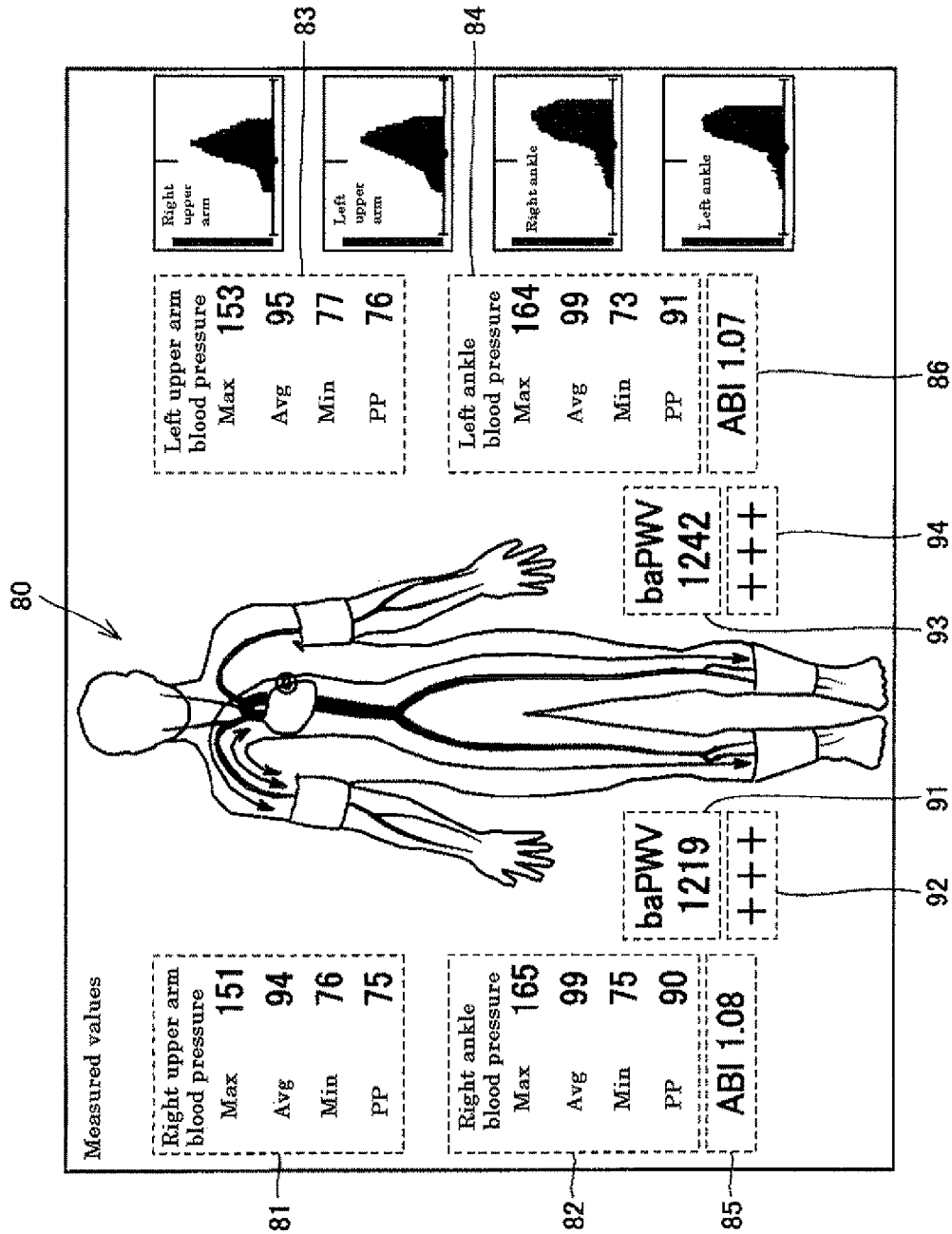
FIG. 8 is a diagram showing an example of an output of analysis result information according to an embodiment of the present invention.

FIG. 8 is a diagram showing an example of an output of analysis result information according to the embodiment of the present invention.

As shown in FIG. 8, printed onto the paper medium as results of the pulse wave analysis are a baPWV_RR value 91, an index 92 indicating the reliability of the baPWV_RR, a baPWV_RL value 93, and an index 94 indicating the reliability of the baPWV_RL. The index indicating reliability is, for example, five levels of signs in order of highest reliability (in order of highest stability), namely "+++", "++", "+", "±", and "−". The five signs to be displayed are stored in advance in the ROM 12 in association with numerical ranges of degrees of stability.

In this way, the indices 92 and 94 indicating reliability are arranged directly under the baPWV values 91 and 93 to which they correspond, and thus these indices are printed in association with the corresponding values. As a result, a healthcare professional such as a physician can make a more accurate diagnosis by giving consideration to not only the baPWV values output as analysis indices, but also the reliability of the indices.

As described above, the pulse wave analysis device 100 of the present embodiment can also measure the blood pressure of each extremity and calculate the ABI_RR and the ABI_RL. Accordingly, a right upper arm blood pressure 81, a right ankle blood pressure 82, a left upper arm blood pressure 83, a left ankle blood pressure 84, an ABI_RR value 85, and an ABI_RL value 86 are furthermore output in FIG. 8.

The units of the baPWV values and the blood pressure values shown in FIG. 8 are "cm/s" and "mmHg" respectively.

The above-described UT and % MAP may also be output as analysis result information. Also, a graph such as that shown in FIG. 9 may be output.

Figure 9:
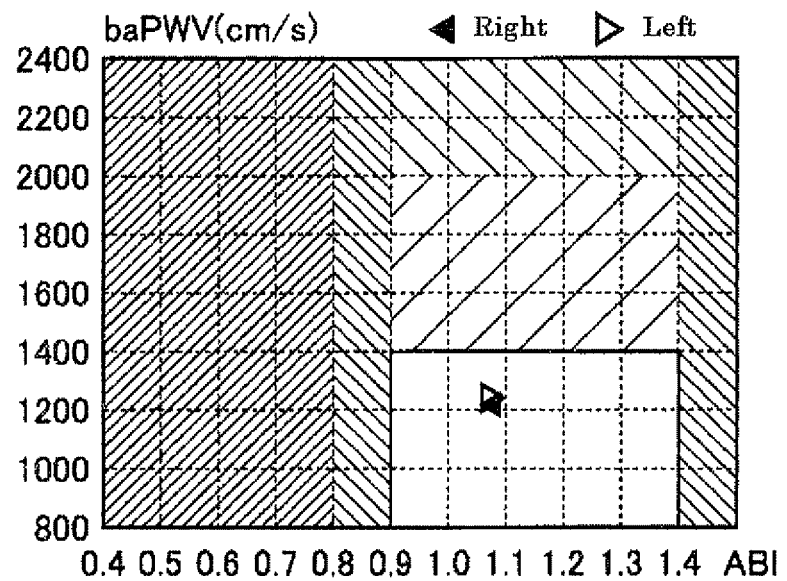
FIG. 9 is a diagram showing another example of an output of analysis result information according to an embodiment of the present invention.

FIG. 9 is a diagram showing another example of an output of analysis result information according to the embodiment of the present invention.

In the graph shown in FIG. 9, the vertical axis indicates baPWV, and the horizontal axis indicates ABI. In this graph, levels of arterial sclerosis determined in advance according to the baPWV and the ABI are shown in an identifiable manner (e.g., by color-coding). In this graph, the levels of arterial sclerosis of the right lower leg and the left lower leg are indicated by predetermined marks, characters, signs, or the like.

In FIG. 9, the level of arterial sclerosis of the right lower leg is indicated by the position of a black triangle mark plotted at the intersection of the baPWV_RR calculated by the analysis processing unit 104 and the ABI_RR calculated by the blood pressure index calculation unit 108. The level of arterial sclerosis of the left lower leg is indicated by the position of a white triangle mark plotted at the intersection of the baPWV_RL calculated by the analysis processing unit 104 and the ABI_RL calculated by the blood pressure index calculation unit 108.

Figure 10:
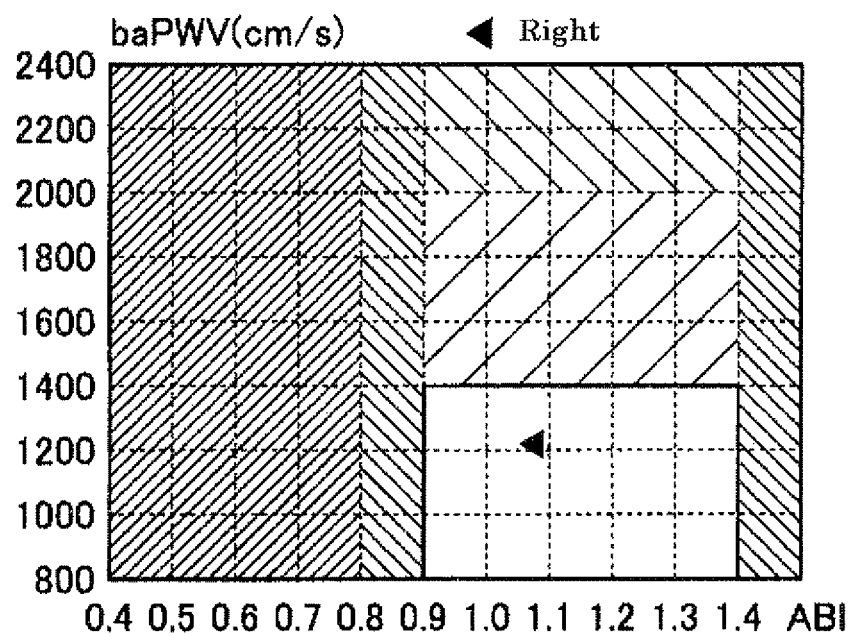
FIG. 10 is a diagram showing yet another example of an output of analysis result information according to an embodiment of the present invention.
Figure 11A:
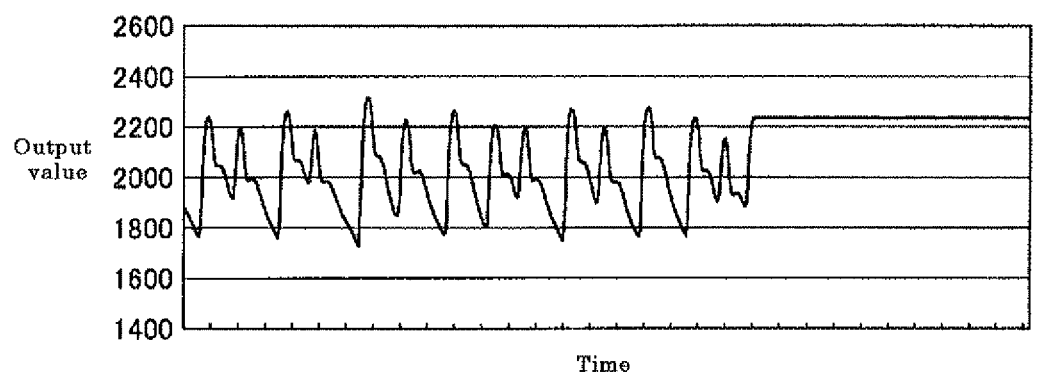
FIG. 11A is a diagram showing a pulse waveform for multiple beats in measurement ID1.
Figure 11B:
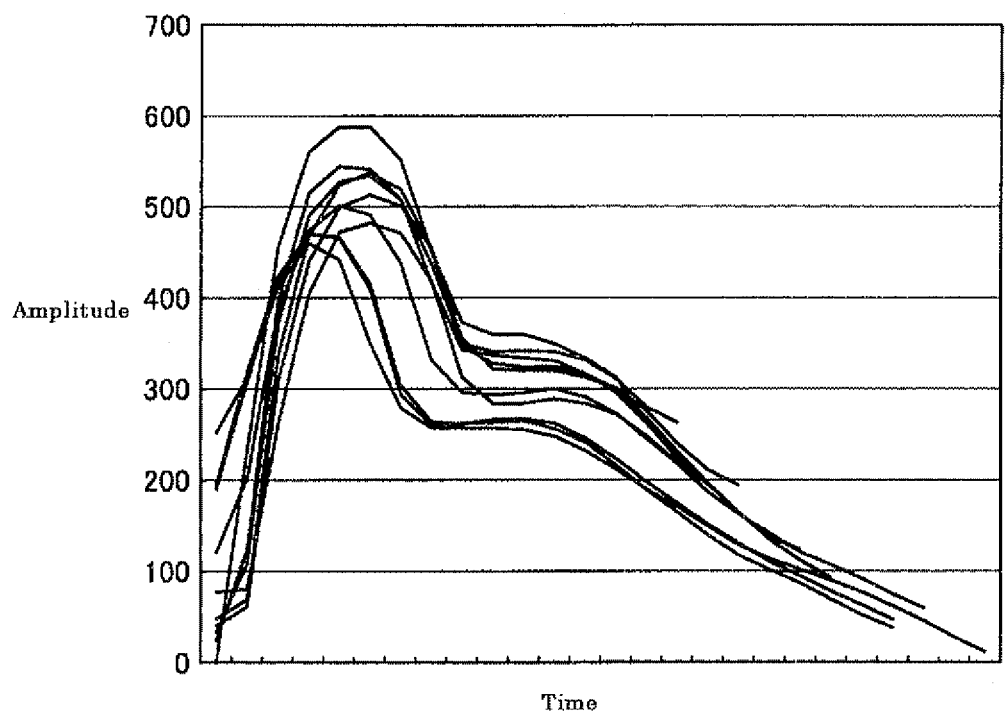
FIG. 11B is a diagram showing the pulse waveform shapes of each beat in FIG. 11A superimposed with each other using the rising position as the origin.
Figure 12A:
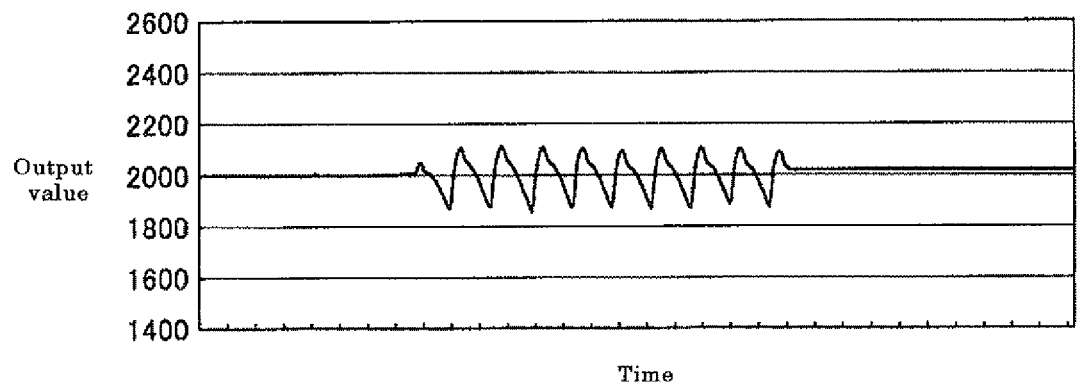
FIG. 12A is a diagram showing a pulse waveform for multiple beats in measurement ID2.
Figure 12B:
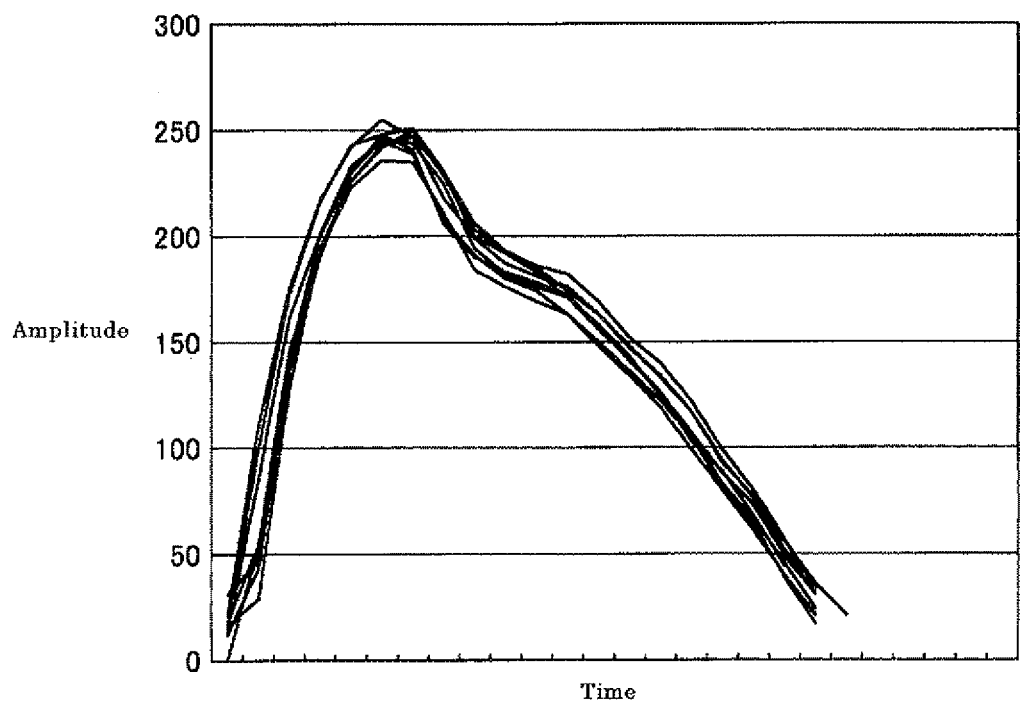
FIG. 12B is a diagram showing the pulse waveform shapes of each beat in FIG. 12A superimposed with each other using the rising position as the origin.
Figure 13A:
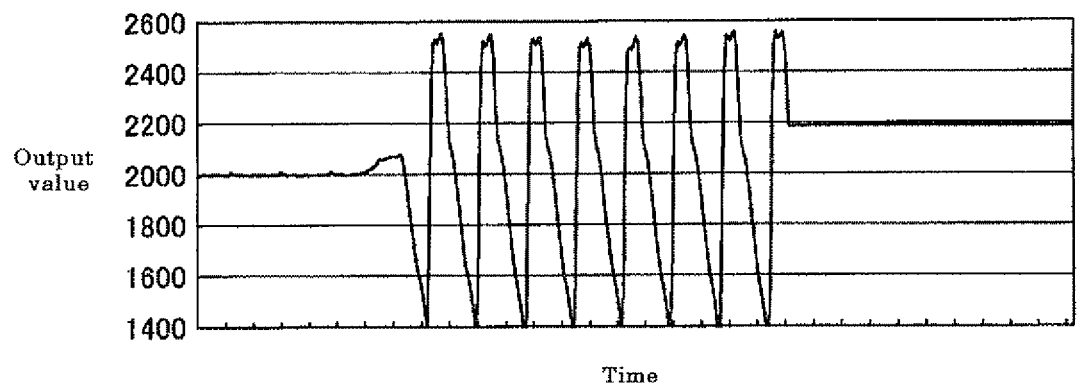
FIG. 13A is a diagram showing a pulse waveform for multiple beats in measurement ID3.
Figure 13B:
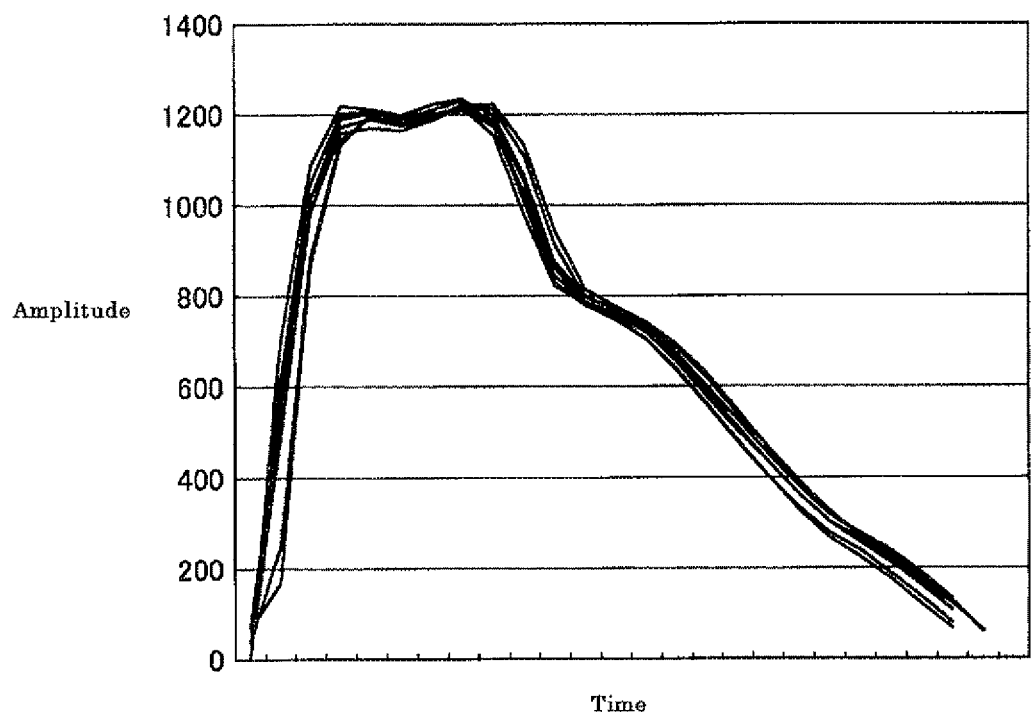
FIG. 13B is a diagram showing the pulse waveform shapes of each beat in FIG. 13A superimposed with each other using the rising position as the origin.
Figure 14A:
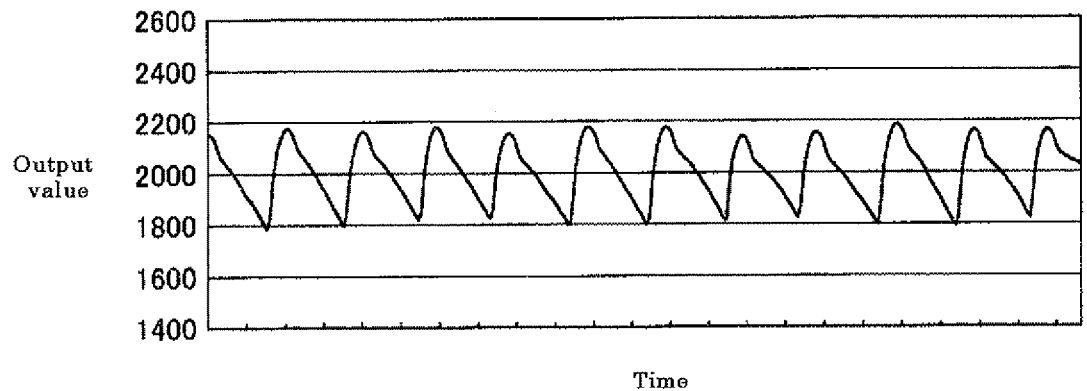
FIG. 14A is a diagram showing a pulse waveform for multiple beats in measurement ID4.
Figure 14B:
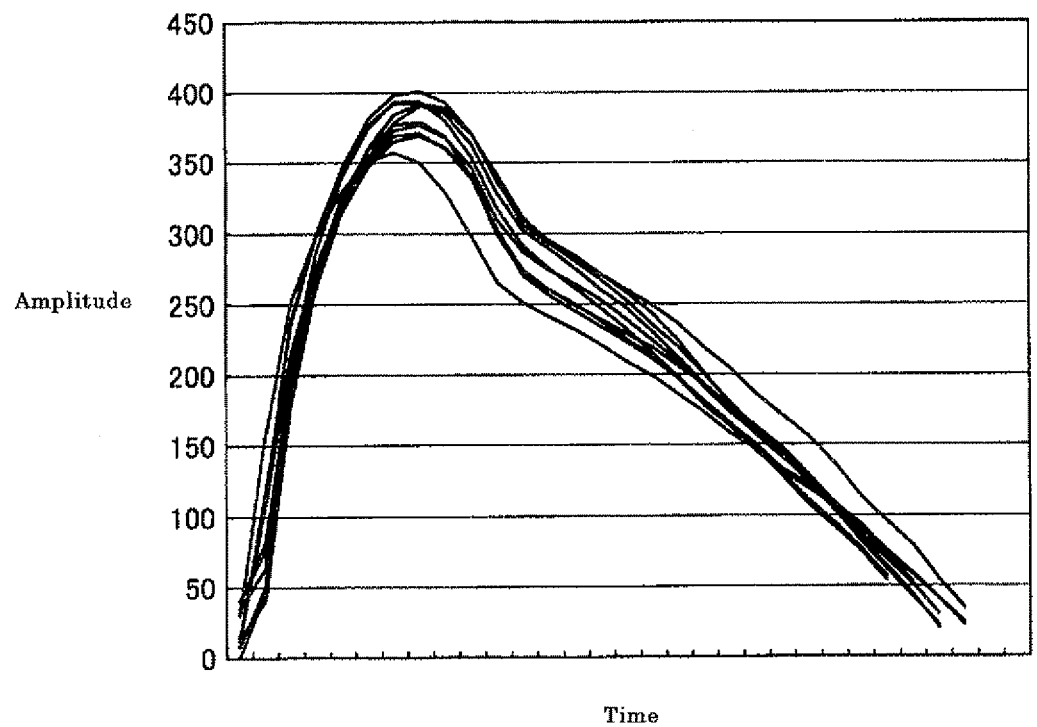
FIG. 14B is a diagram showing the pulse waveform shapes of each beat in FIG. 14A superimposed with each other using the rising position as the origin.
Figure 15A:
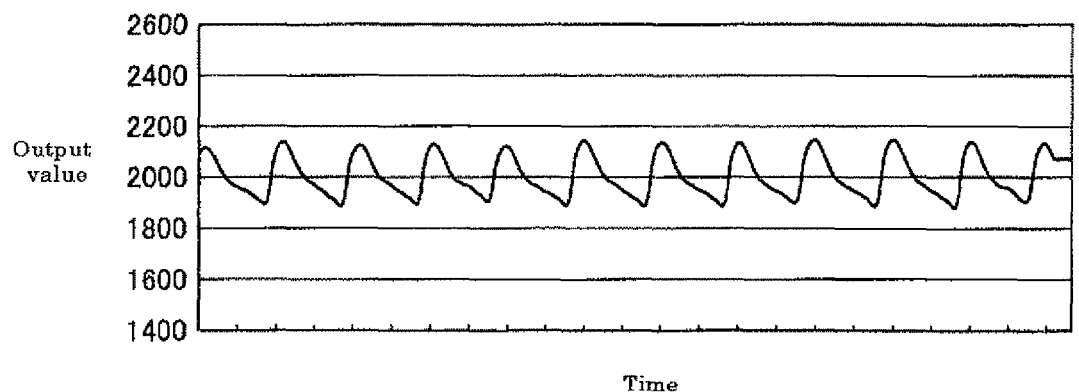
FIG. 15A is a diagram showing a pulse waveform for multiple beats in measurement ID5.
Figure 15B:
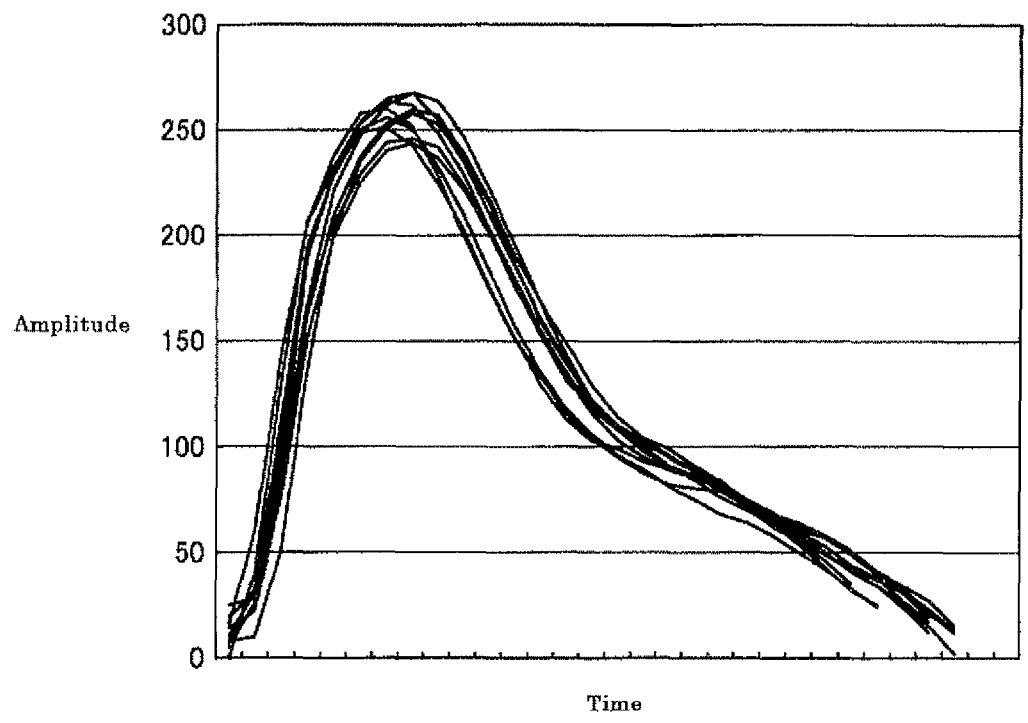
FIG. 15B is a diagram showing the pulse waveform shapes of each beat in FIG. 15A superimposed with each other using the rising position as the origin.
Figure 16A:
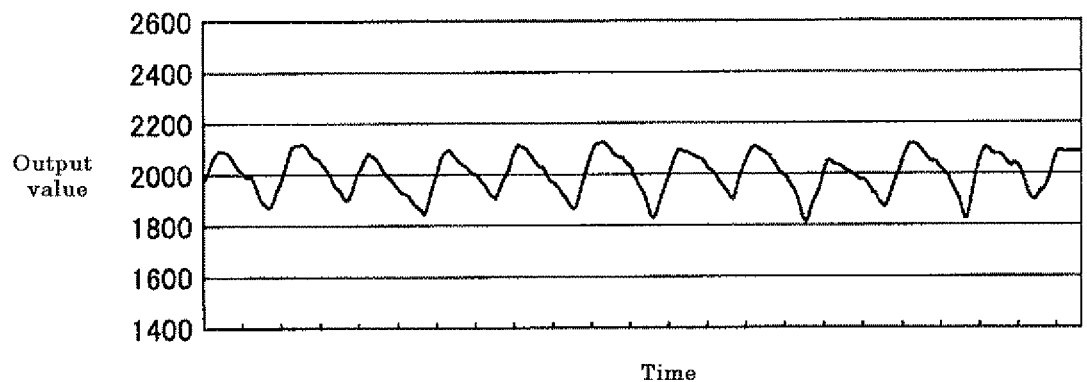
FIG. 16A is a diagram showing a pulse waveform for multiple beats in measurement ID6.
Figure 16B:
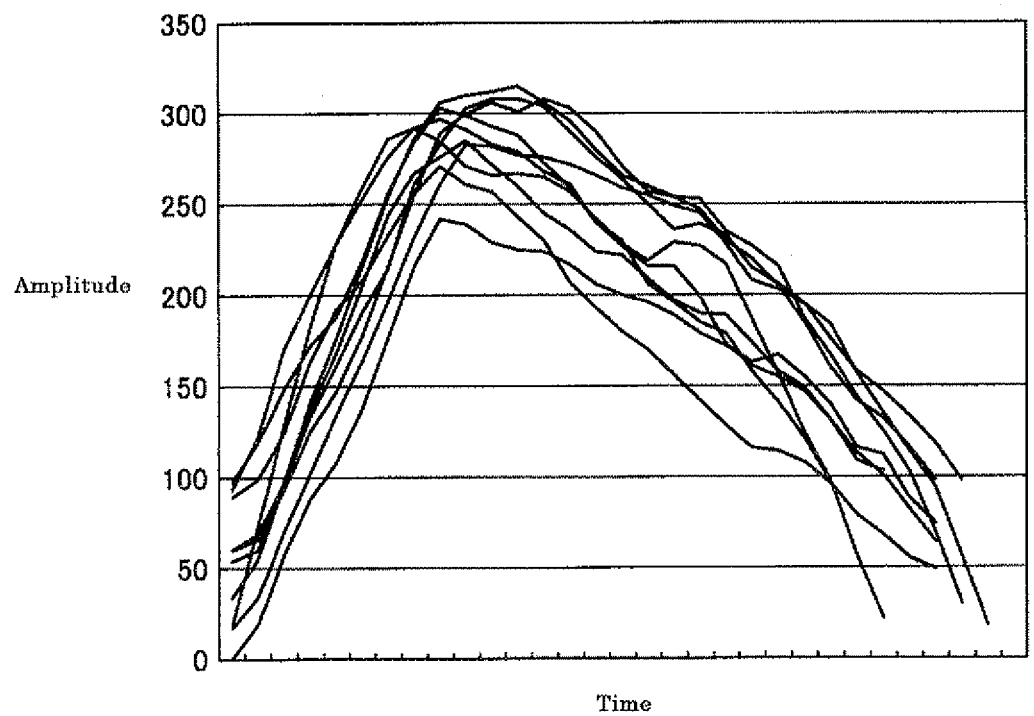
FIG. 16B is a diagram showing the pulse waveform shapes of each beat in FIG. 16A superimposed with each other using the rising position as the origin.
Figure 17A:
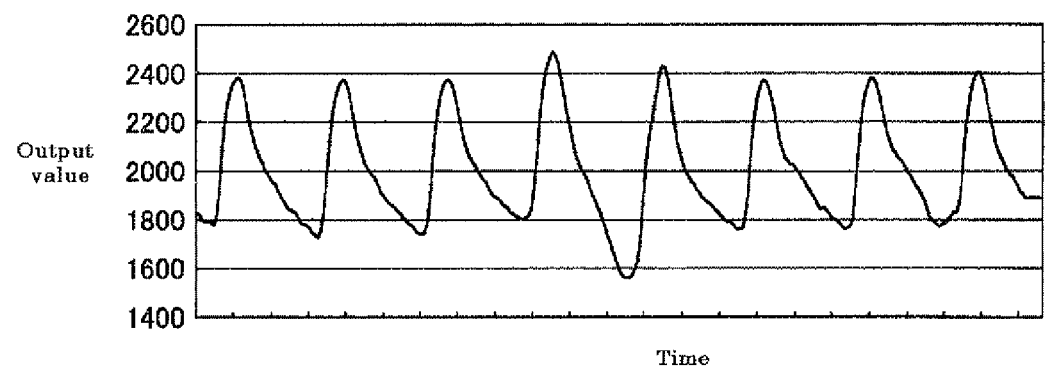
FIG. 17A is a diagram showing a pulse waveform for multiple beats in measurement ID7.
Figure 17B:
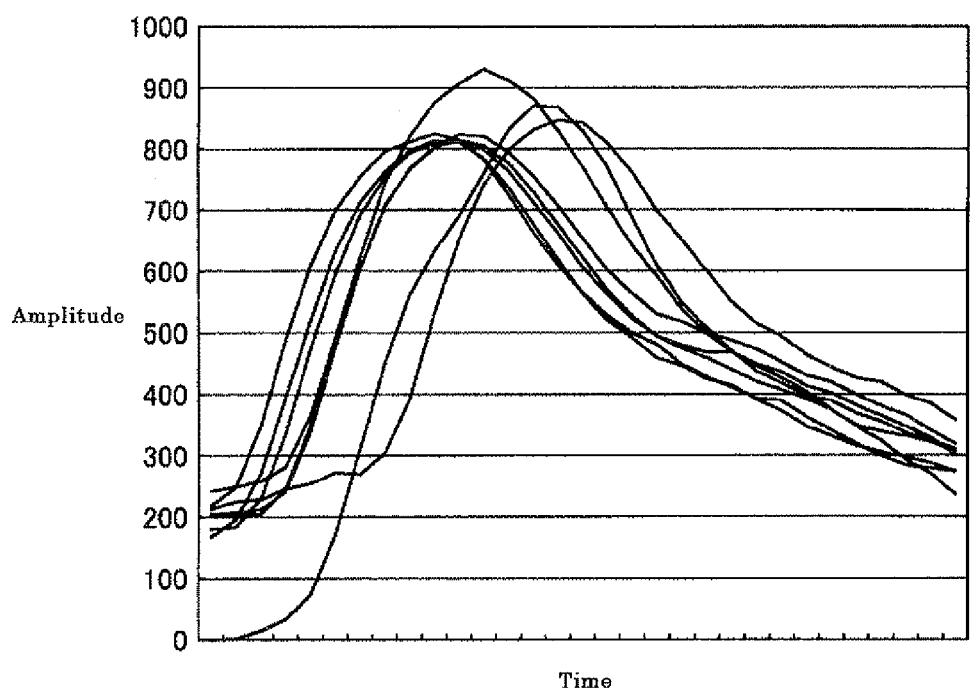
FIG. 17B is a diagram showing the pulse waveform shapes of each beat in FIG. 17A superimposed with each other using the rising position as the origin.
Figure 18A:
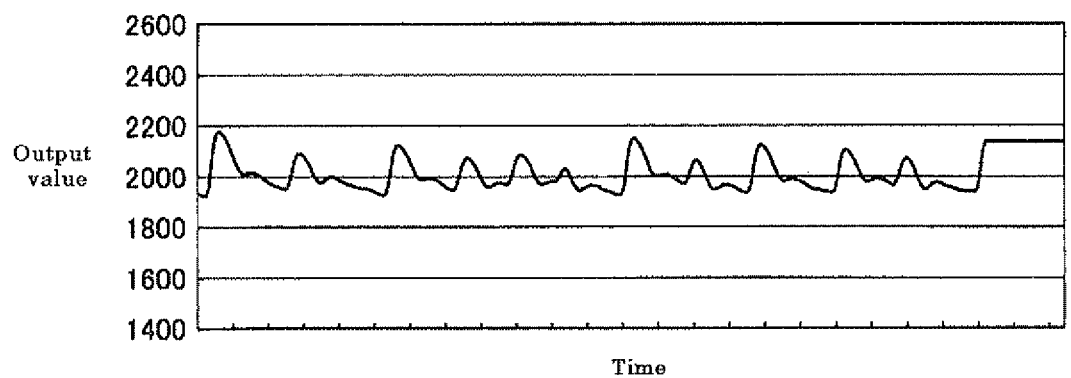
FIG. 18A is a diagram showing a pulse waveform for multiple beats in measurement ID8.
Figure 18B:
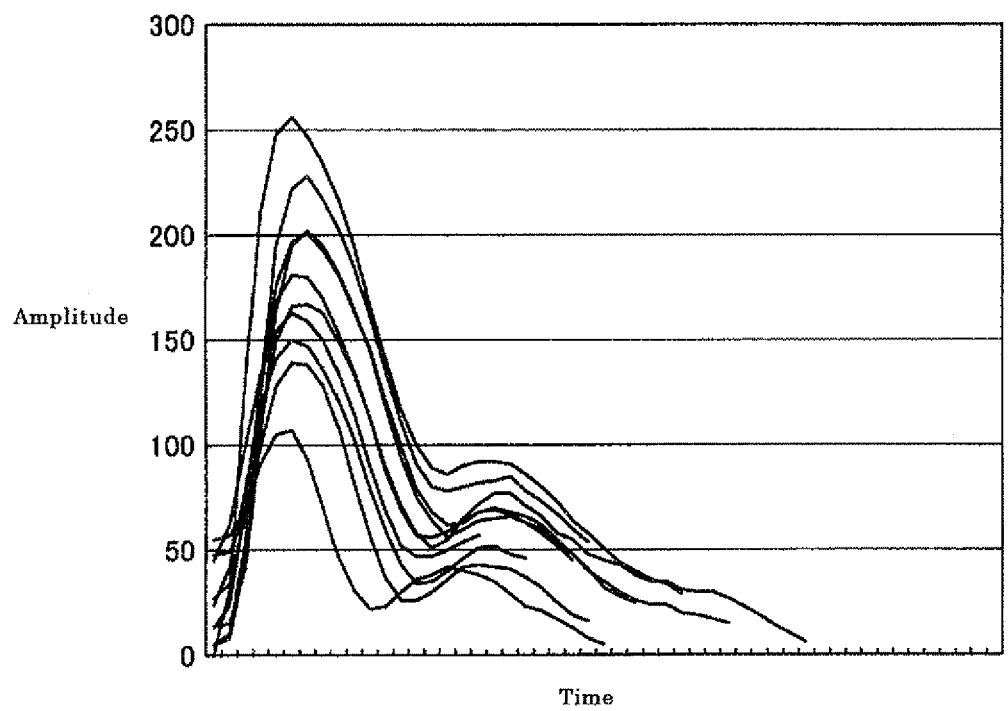
FIG. 18B is a diagram showing the pulse waveform shapes of each beat in FIG. 18A superimposed with each other using the rising position as the origin.
Figure 19A:
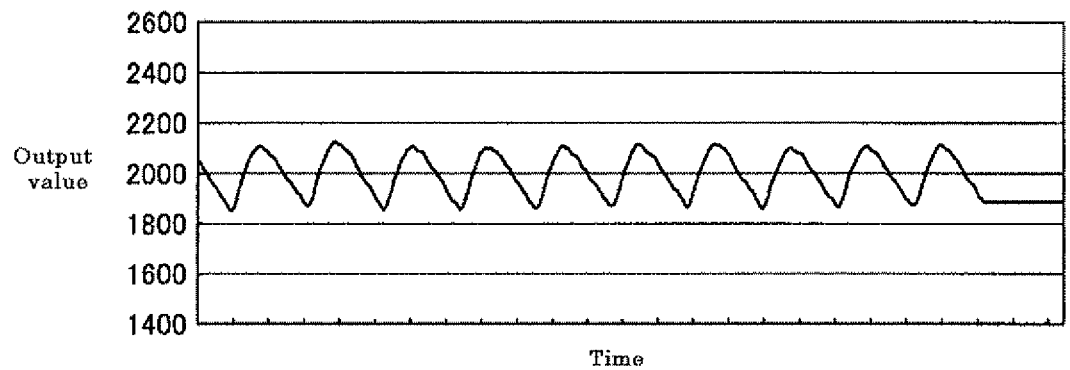
FIG. 19A is a diagram showing a pulse waveform for multiple beats in measurement ID9.
Figure 19B:
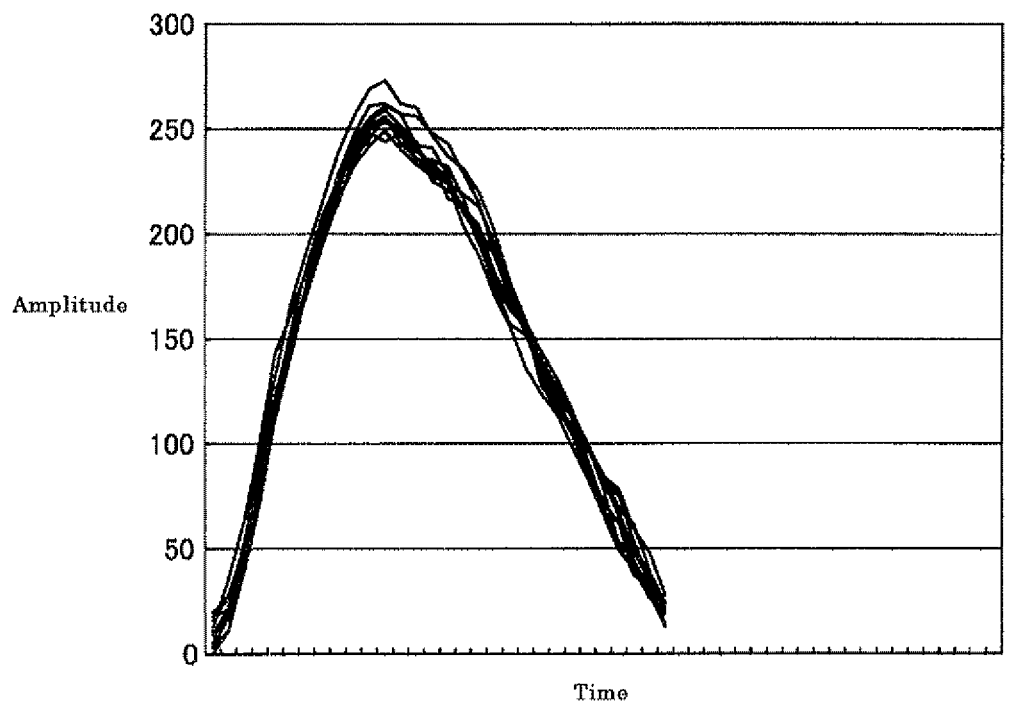
FIG. 19B is a diagram showing the pulse waveform shapes of each beat in FIG. 19A superimposed with each other using the rising position as the origin.
Figure 20A:
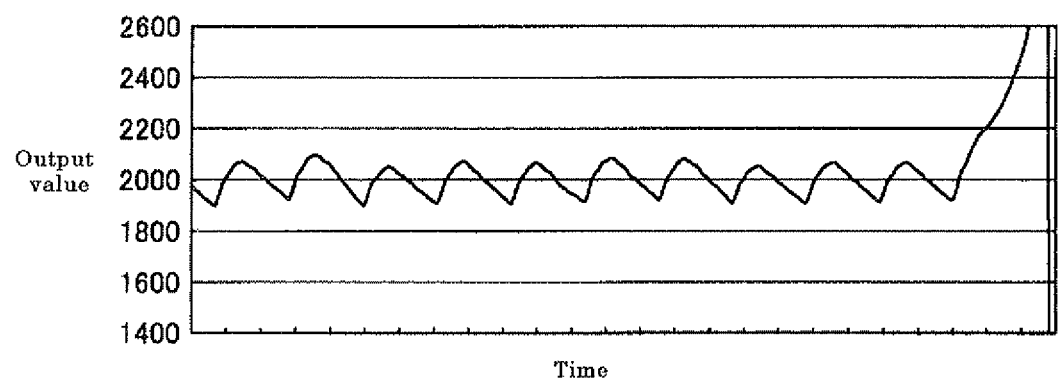
FIG. 20A is a diagram showing a pulse waveform for multiple beats in measurement ID10.
Figure 20B:
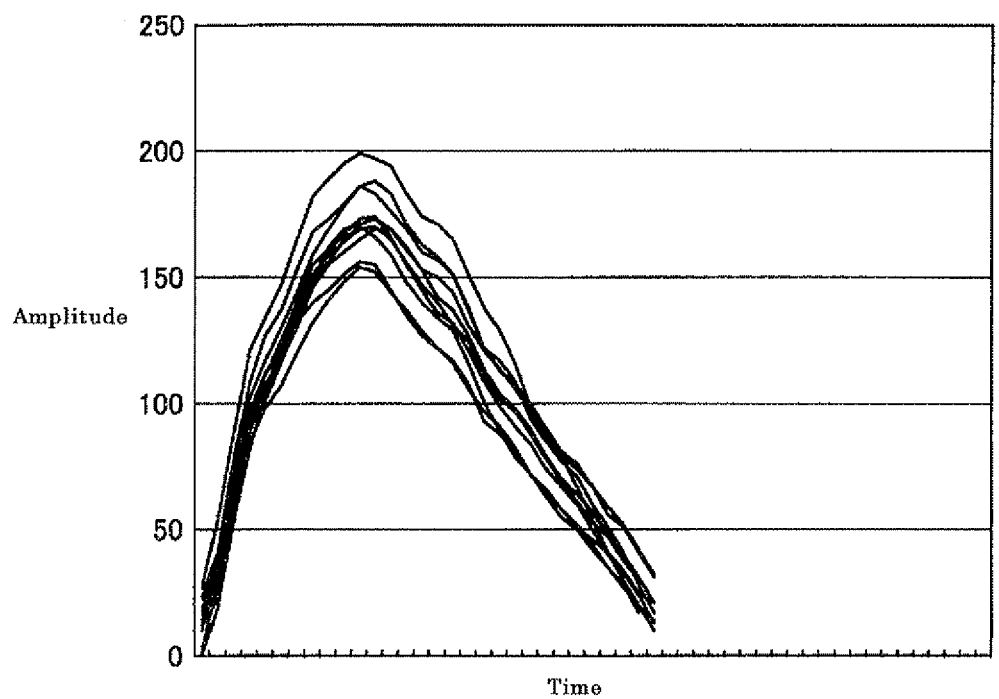
FIG. 20B is a diagram showing the pulse waveform shapes of each beat in FIG. 20A superimposed with each other using the rising position as the origin.
Figure 21A:
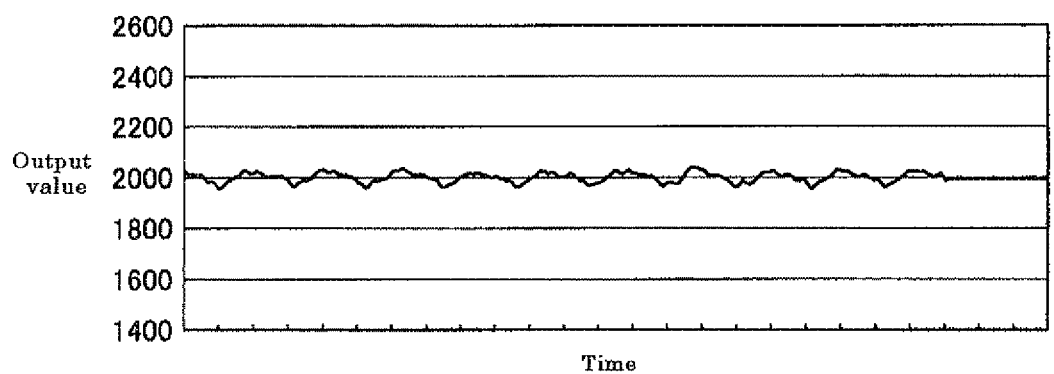
FIG. 21A is a diagram showing a pulse waveform for multiple beats in measurement ID11.
Figure 21B:
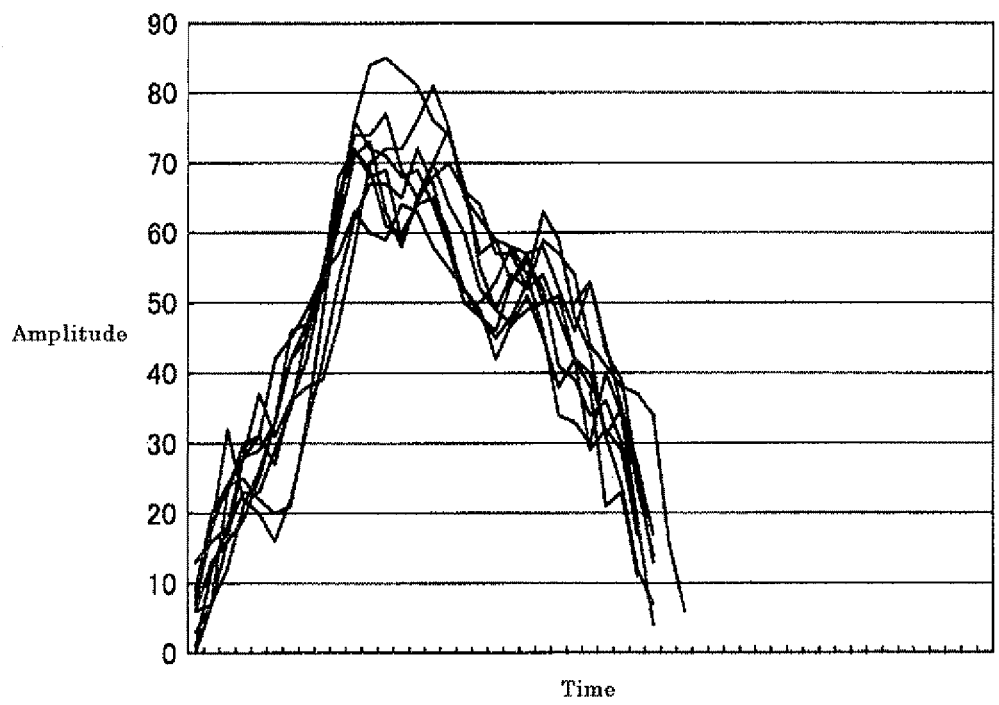
FIG. 21B is a diagram showing the pulse waveform shapes of each beat in FIG. 21A superimposed with each other using the rising position as the origin.
Figure 22A:
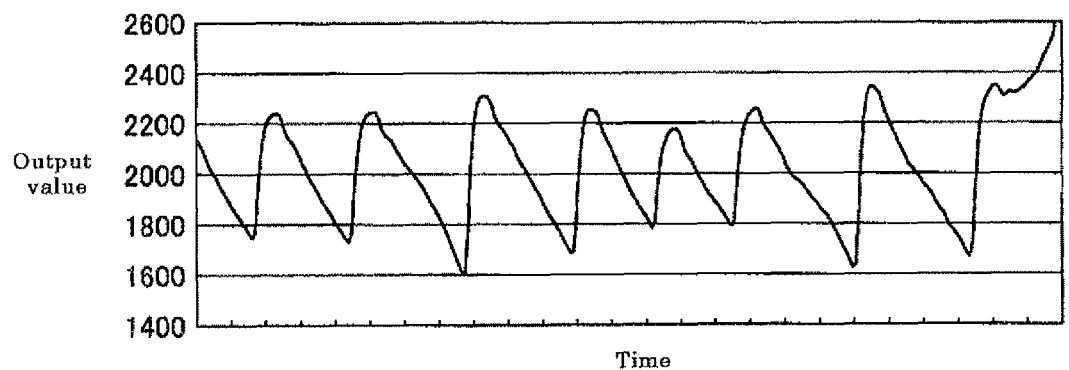
FIG. 22A is a diagram showing a pulse waveform for multiple beats in measurement ID12.
Figure 22B:
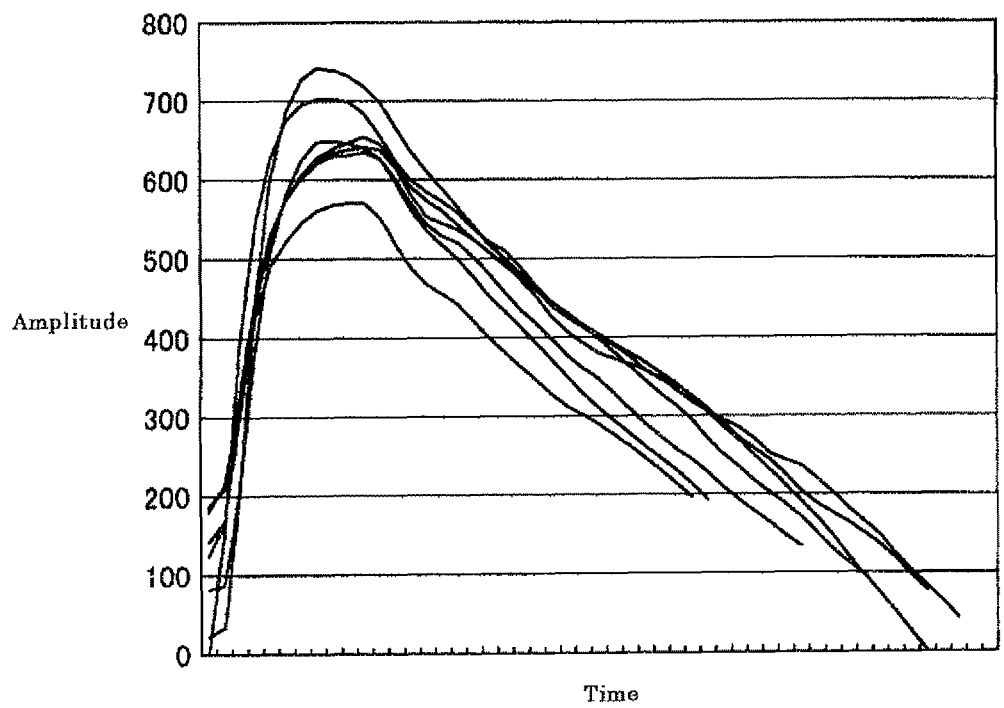
FIG. 22B is a diagram showing the pulse waveform shapes of each beat in FIG. 22A superimposed with each other using the rising position as the origin.
Figure 23A:
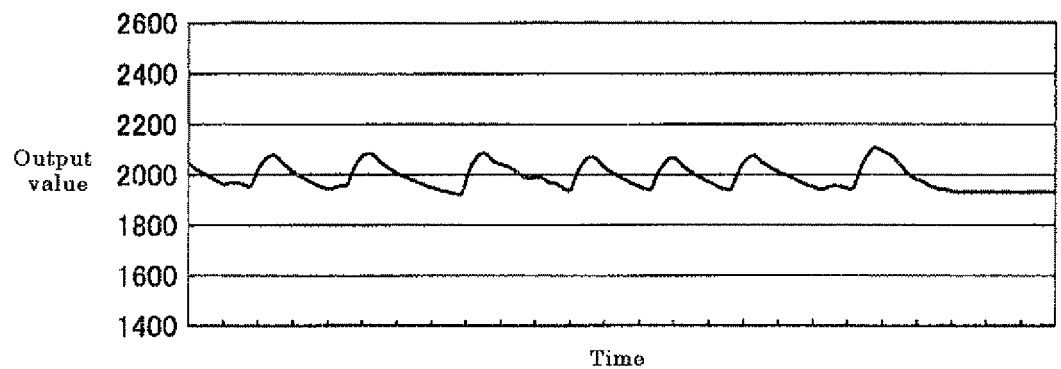
FIG. 23A is a diagram showing a pulse waveform for multiple beats in measurement ID13.
Figure 23B:
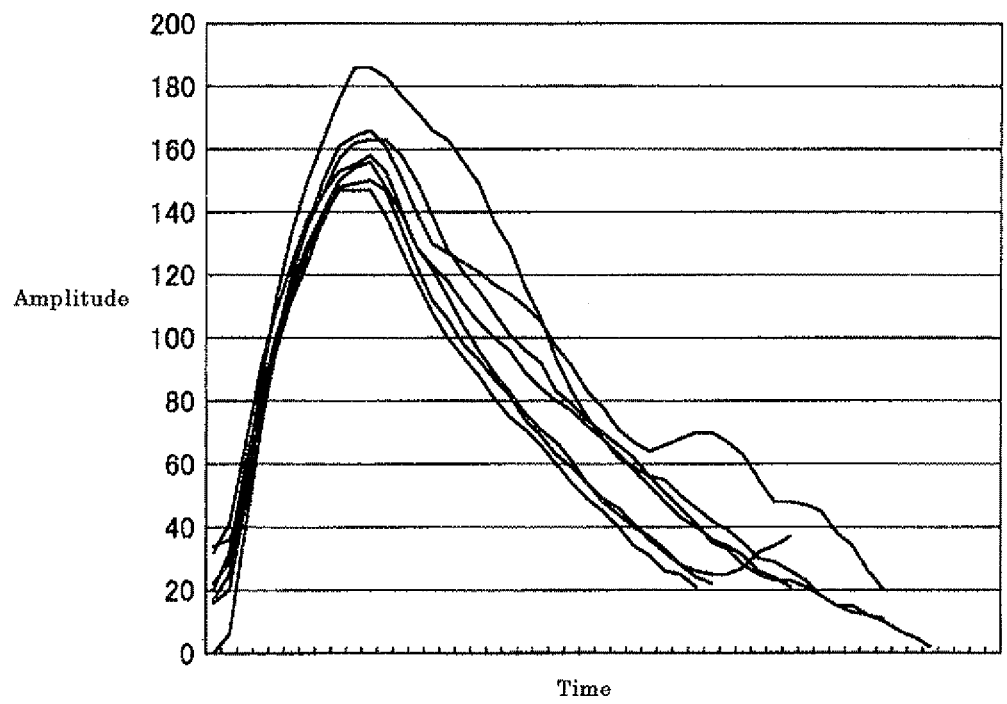
FIG. 23B is a diagram showing the pulse waveform shapes of each beat in FIG. 23A superimposed with each other using the rising position as the origin.
Figure 24A:
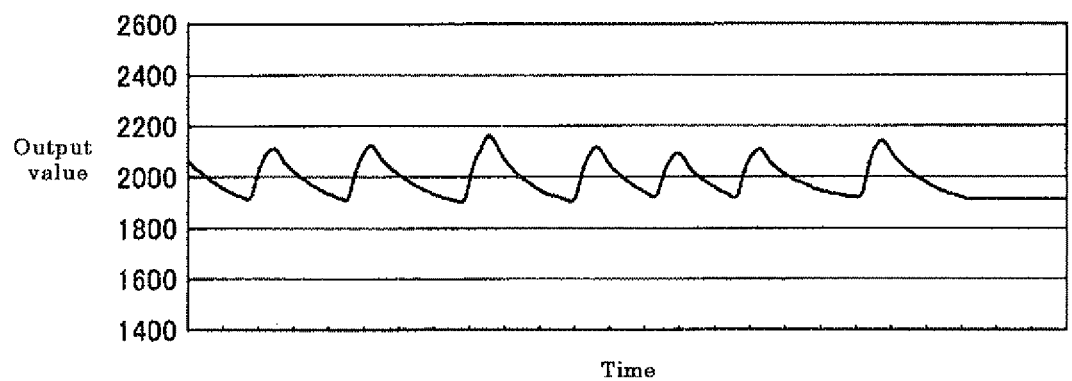
FIG. 24A is a diagram showing a pulse waveform for multiple beats in measurement ID14.
Figure 24B:
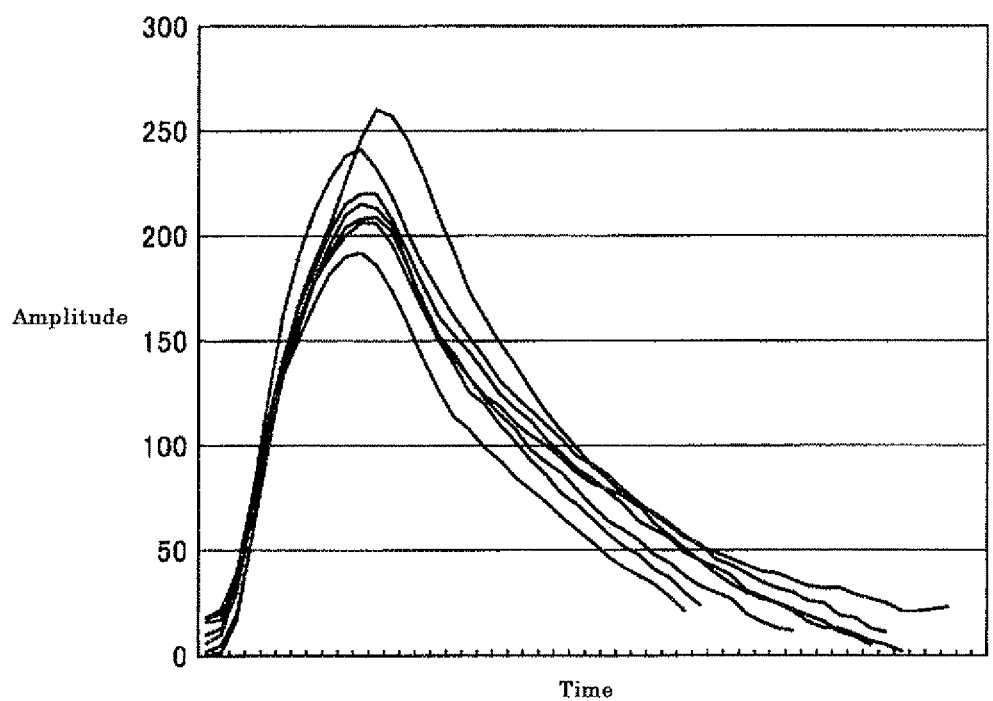
FIG. 24B is a diagram showing the pulse waveform shapes of each beat in FIG. 24A superimposed with each other using the rising position as the origin.
Figure 25A:
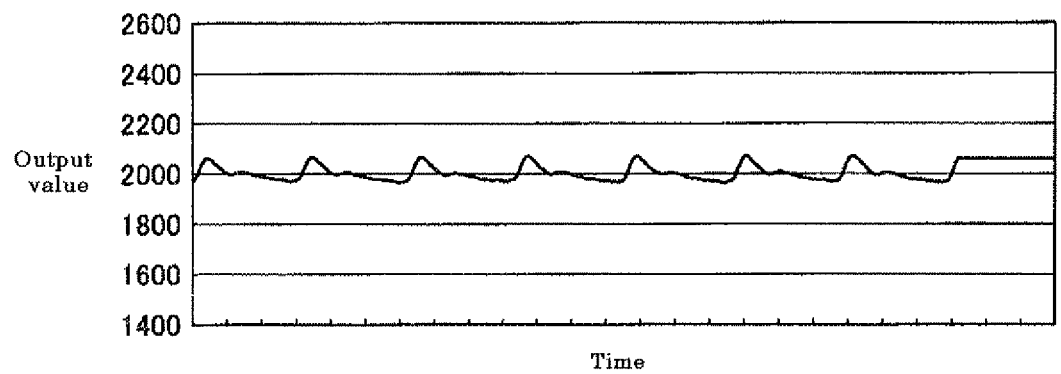
FIG. 25A is a diagram showing a pulse waveform for multiple beats in measurement ID15.
Figure 25B:
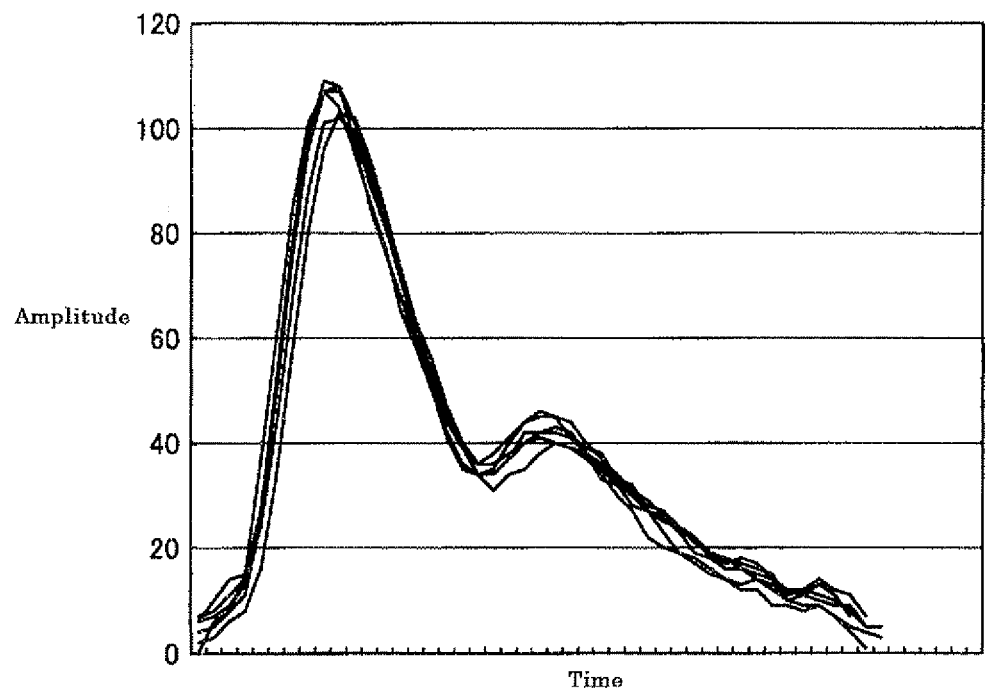
FIG. 25B is a diagram showing the pulse waveform shapes of each beat in FIG. 25A superimposed with each other using the rising position as the origin.
Figure 26A:
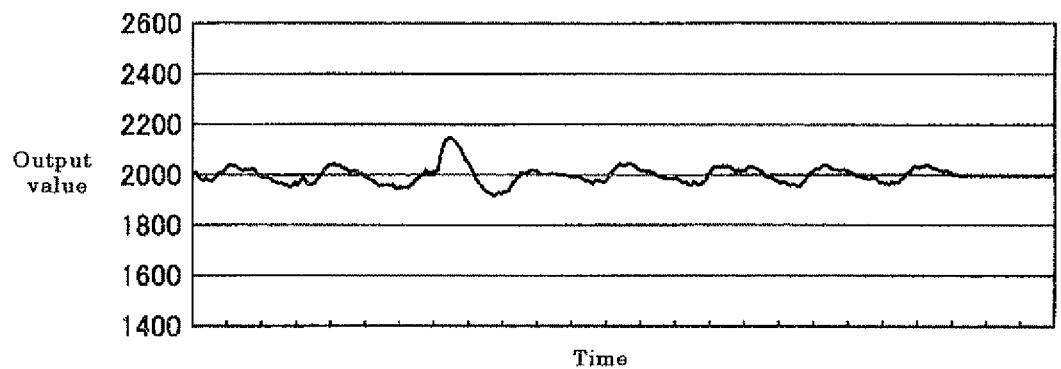
FIG. 26A is a diagram showing a pulse waveform for multiple beats in measurement ID16.
Figure 26B:
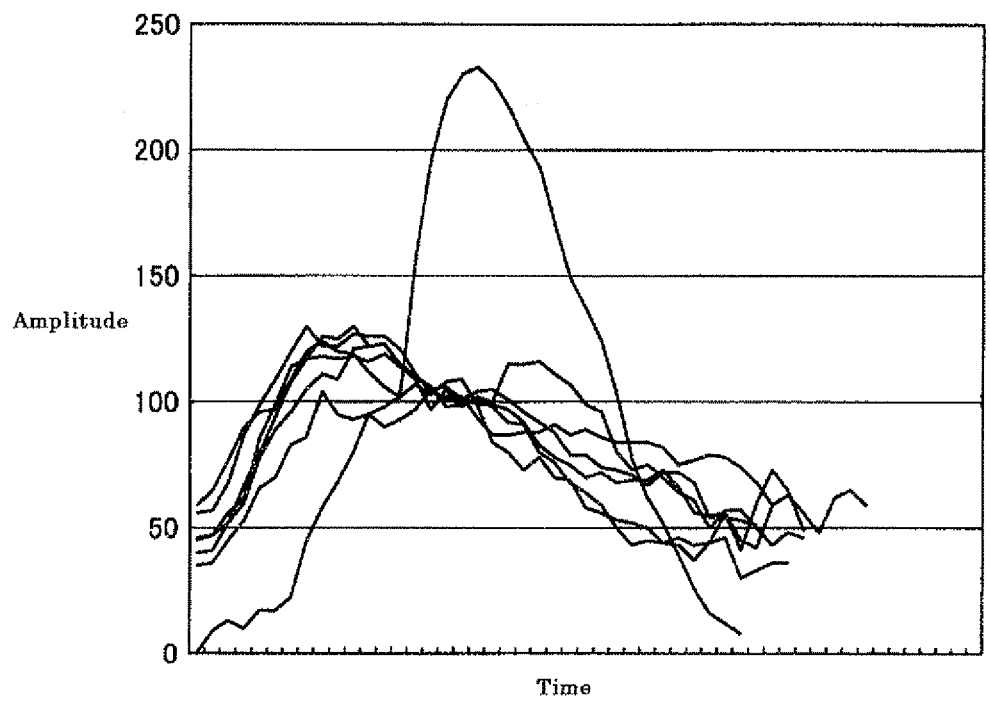
FIG. 26B is a diagram showing the pulse waveform shapes of each beat in FIG. 26A superimposed with each other using the rising position as the origin.
Figure 27A:
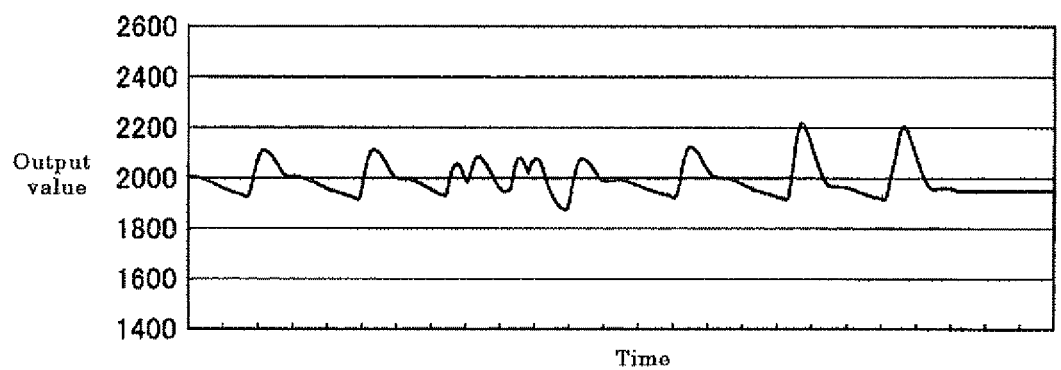
FIG. 27A is a diagram showing a pulse waveform for multiple beats in measurement ID17.
Figure 27B:
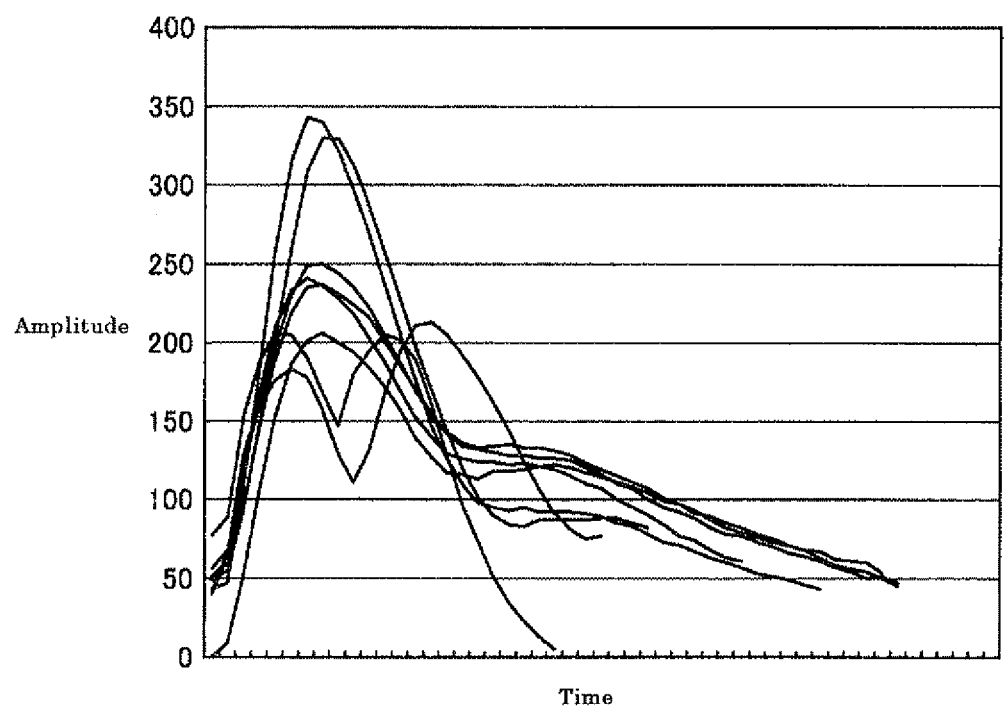
FIG. 27B is a diagram showing the pulse waveform shapes of each beat in FIG. 27A superimposed with each other using the rising position as the origin.

Note that in the present embodiment, both the measured baPWV_RR and baPWV_RL are output as analysis result information. However, between the measured baPWV_RR and baPWV_RL, it is possible to output only the baPWV that has the higher reliability (stability) calculated in step S112 in FIG. 6 as the pulse wave analysis results. For example, since generally only brief information is printed on a report to be presented to the patient, a configuration is possible in which only one baPWV is printed for only the report for the patient. In such a case, a graph such as that shown in FIG. 10 may be printed instead of the graph shown in FIG. 9. In the graph shown in FIG. 10, the vertical axis indicates baPWV, the horizontal graph indicates ABI, and only the baPWV with the higher stability is plotted. In this way, by outputting only the baPWV with the higher reliability (stability), it is possible to make a determination or diagnosis that is more appropriate than the case where simply the baPWV with the higher value or the average value of the left and right baPWV is plotted.

Expression for Calculating Degree of Approximation

As described above, in the present embodiment, degrees of approximation between an integrated pulse wave and each beat are used in order to precisely calculate an analysis index. The expression for calculating the degree of approximation can be appropriately determined through experimentation.

FIGS. 11A to 27B are diagrams showing examples in which the pulse waveform shapes of each beat are superimposed with each other using the rising position as the origin, for measurements ID1 to ID17 respectively. In FIGS. 11A to 27A, a measured pulse waveform for multiple beats is indicated along a time axis, and in FIGS. 11B to 27B, the pulse waveform shapes of each beat shown in FIGS. 11A to 27A are shown superimposed with each other using the rising position as the origin. The values indicated by the vertical axis in FIGS. 11A to 27A represent output values obtained by performing digital conversion on pressure values, and the values indicated by the vertical axis in FIGS. 11B to 27B represent the amplitude. Also, the separators on the horizontal axis in FIGS. 11B to 27B represent sampling points.

FIG. 28 is a diagram showing the relationship between the order of degrees of approximation calculated by a device and the order of degrees of approximations made by the observer in the case of targeting the pulse waveforms of FIGS. 11A to 27B.

In FIG. 28, for each measurement ID, "Index" indicates a percentage obtained by applying a predetermined conversion expression to the average value of the degrees of approximation of each beat (with respect to an integrated shape that is not shown) calculated by the above-described Expression (1). Also, "Device order" indicates the indices represented as percentages in order or highest percentage. Also, for each measurement ID, "Observer order" indicates the order of the average value of the degrees of approximation of each beat (with respect to an integrated shape that is not shown) determined in accordance with a manual by a user having sufficient knowledge regarding pulse waves, such as a healthcare professional or the developer of the pulse wave analysis device 100.

Figure 29:
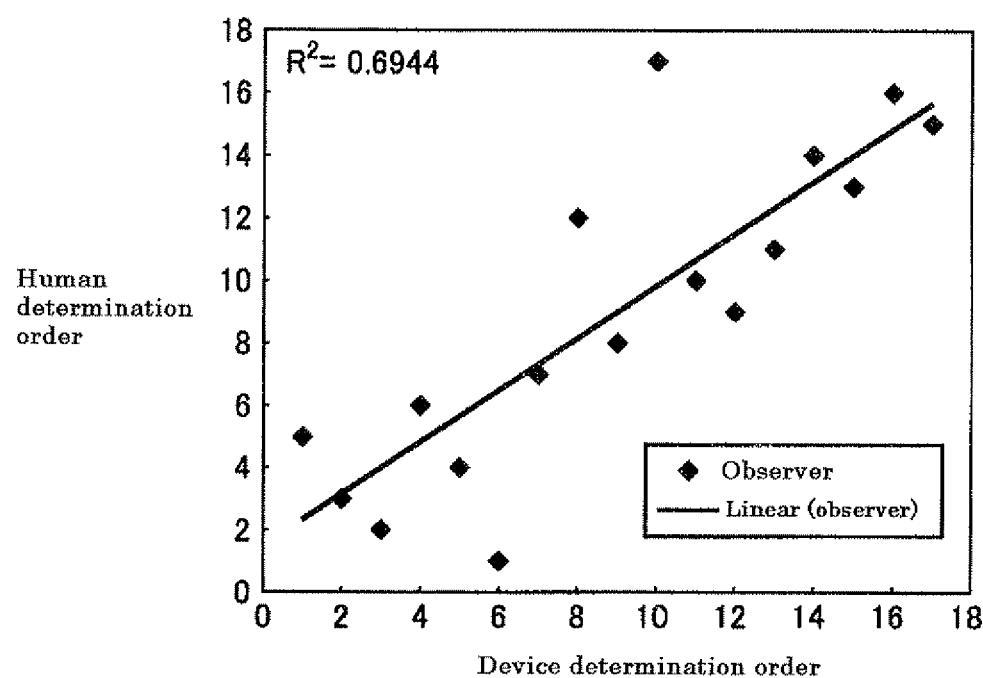
FIG. 29 is a diagram showing the correlation between the order of approximations calculated by the device and the order of approximations made by the observer shown in FIG. 28.

FIG. 29 is a diagram showing the correlation between the order of approximation obtained by device and the order of approximation obtained by the observer shown in FIG. 28. As shown in FIG. 29, when "Human determination order (observer order)" is indicated on the Y axis and "Device determination order" is indicated on the X axis in a two-dimensional coordinate plane, a coefficient of determination $R^2$ of the correlation between the two is expressed as 0.6844.

In this way, in the case of calculating degrees of approximation using the above-described Expression (1), although results close to the observer order can be obtained, it is desirable for the expression for calculating the degree of approximation to be determined, through experimentation, as an expression according to which the observer order and the device determination order match, that is to say, an expression according to which the coefficient of determination $R^2$ approaches 1.0. This is because disruption of a waveform (arrhythmia or body movement) has conventionally been determined visually by a person such as a healthcare professional.

Variation 1

In the above embodiment, in the case of calculating the baPWV, the arm on the side determined as being the default (e.g., the right arm) is used as the upper arm measurement site. Alternatively, whether the right upper arm or the left upper arm is to be used in the baPWV calculation is determined according to a blood pressure difference between the right upper arm and the left upper arm.

However, the upper arm measurement site to be used in baPWV calculation may be determined based on the degrees of approximation calculated by the analysis processing unit 104.

Specifically, processing such as the following may be performed in step S110 (calculation of pulse wave velocity) in FIG. 6. In the following description as well, it is assumed that it has been determined that by default the pulse wave of the right upper arm is to be used in baPWV calculation.

In the immediately previous step S108 (exclusion processing), the analysis processing unit 104 determines whether the average value "AVr" of the degrees of approximation of the beats "BTr" that were not excluded as calculation targets among the pulse waves of the right upper arm is greater than or equal to a predetermined threshold value. In the case of determining that the average value AVr is less than the threshold value, the left upper arm pulse waves are used in baPWV calculation. Also, a configuration is possible in which the user is notified to redo the measurement if the average value "AVl" of the degrees of approximation of the beats "BTl" that were not excluded as calculation targets among the pulse waves of the left upper arm is less than the predetermined threshold value.

Also, the average value AVr and the average value AVl may be compared, and the pulse waves of the site for which the value is higher may be used in baPWV calculation.

Taking FIG. 7 as an example, the beats BTr are the beats other than the 3rd beat for which the degree of approximation with the integrated pulse wave of the right upper arm was low. Also, giving consideration to the exclusion results for the ankle pulse waves as well, the beats BTr may be the beats other than the 3rd, 5th, and 6th beats. Similarly, the beats BTl are the beats other than the 4th beat for which the degree of approximation with the integrated pulse wave of the left upper arm was low. Also, giving consideration to the exclusion results for the ankle pulse waves as well, the beats BTl may be the beats other than the 4th to 6th beats.

For the ankle pulse waves as well, similarly to the upper arm pulse waves, a configuration is possible in which only either the left or right pulse waves are used in baPWV calculation, and only one baPWV is calculated using the stable upper arm pulse waves and ankle pulse waves.

Variation 2

Although the baPWV_RL and the baPWV_RR are measured in the above embodiment, the PWV may be a PWV that can be calculated from pulse waves at one measurement site.

Figure 30:
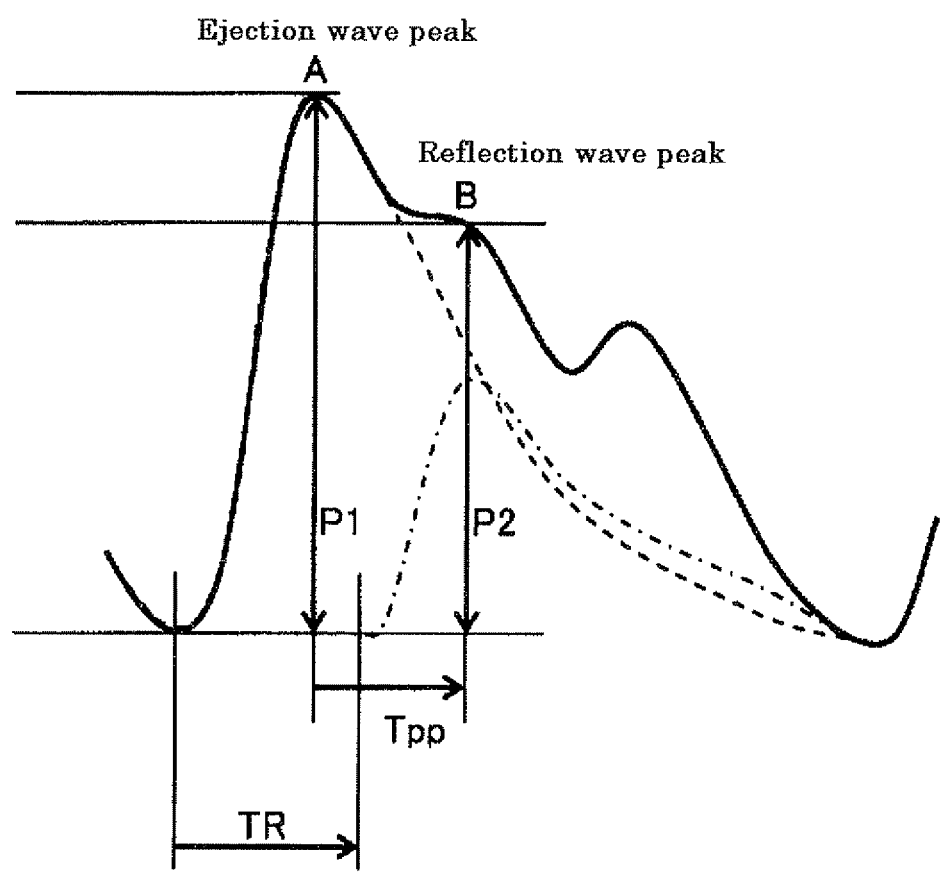
FIG. 30 is a diagram for illustrating a method of calculating a pulse wave analysis index according to another embodiment of the present invention.

In the case of calculating a PWV from pulse waves at one measurement site, the PWV is obtained by dividing the pulse wave transit distance (Lpt) by the pulse transit time (PTT). The transit distance is the so-called "trunk length", and is double the distance between the heart and the bifurcation of the iliac artery, which is the reflection site. The trunk length is a length proportional to the body height. Although the pulse wave transit distance cannot be directly measured, it can be obtained using a predetermined conversion expression. PTT is calculated by applying Tpp and TR shown in FIG. 30 to a predetermined conversion expression. Tpp represents the time interval from when the peak (maximum point) of the ejection wave, which is the traveling wave, appears to when the peak (maximum point) of the reflection wave appears. TR represents the time interval from when the ejection wave appears to when the reflection wave appears as a result of the traveling wave being reflected off the bifurcation of the iliac artery and returning. These values can also be used as indices for determining the degree of arterial sclerosis. In FIG. 30, Tpp is represented by the time interval from point A, which is the ejection wave peak point, to point B, which is the reflection wave peak point. In FIG. 30, TR is represented by the time interval from the rising point of the ejection wave to the rising point of the reflection wave.

Also, an AI may be calculated as the analysis index. In this case, as shown in FIG. 30, the analysis processing unit (104) extracts the amplitude P2 at point B with respect to the amplitude P1 at point A, and obtains an AI value by dividing the amplitude P1 by the amplitude P2.

In the case of calculating such a PWV or AI as the analysis index, a configuration is possible in which the range influencing index calculation is limited to the range from the pulse rising point to the reflection wave peak when calculating the degree of approximation.

Variation 3

Although the pulse wave analysis device 100 is described as including the detection units 20, the cuffs 24, and the information processing unit 1 in the above embodiments, the pulse wave analysis device may be realized in an ordinary computer that does not include the detection units 20 or the cuffs 24. Specifically, in the present embodiment, the pulse wave analysis device can realize pulse wave analysis processing such as that shown in FIG. 6 as long as it includes the functionality of the analysis processing unit 104, which is typically realized by the CPU 10. The ordinary computer needs only have hardware similar to that of the information processing unit 1.

A pulse wave analysis method performed by the pulse wave analysis devices of the present embodiment and the variations can be provided as a program. Such a program is recorded on a computer-readable non-transitory recording medium. Examples of a computer-readable recording medium include an optical medium such as a CD-ROM (Compact Disc-ROM), and a magnetic recording medium such as a memory card. Also, such a program can be recorded on a computer-readable recording medium and provided as a program product. The program can also be provided by downloading via a network.

Note that the program according to the present embodiment may invoke necessary modules, among program modules provided as part of a computer operating system (OS), in a predetermined sequence at predetermined timings, and cause such modules to execute processing. In this case, processing is executed in cooperation with the OS, without the above modules being included in the program itself. Such a program that does not include modules can also be the program according to the present embodiment.

Also, the program according to the present embodiment may be provided incorporated in part of another program. In this case as well, processing is executed in cooperation with the other program, without the modules included in the other program being included in the program itself. Such a program incorporated in another program can also be the program according to the present embodiment.

The program product that is provided is executed after being installed in a program storage unit such as a hard disk. Note that the program product includes the program itself and the storage medium on which the program is stored.

The embodiments of the invention described above are to be considered in all respects only as illustrative and not restrictive. The scope of the invention is indicated by the appended claims rather than the above description, and all changes which come within the meaning and range of equivalency of the claims are to be embraced within the scope of the invention.

INDUSTRIAL APPLICABILITY

A pulse wave analysis device is provided that can calculate a pulse wave analysis index using only stable beats including little influence from body movement and the like.

The invention claimed is:

1. A pulse wave analysis device comprising:
    a storage unit for storing a pulse waveform for a plurality of beats;
    an analysis processing unit configured to:
        (1) integrate pulse waveform shapes of each beat that constitute the pulse waveform for the plurality of beats by combining the plurality of beats so as to obtain an integrated pulse waveform shape,
        (2) determine a degree of approximation between the integrated pulse waveform shape and each of the plurality of beats,
        (3) calculate a pulse wave analysis index for the plurality of beats after excluding, as a calculation target, a beat for which the degree of approximation between the integrated pulse waveform shape and the pulse waveform shape of the beat is low, and
        (4) calculate a degree of stability of beating by integrating the degrees of approximation of each pulse waveform shape used in the calculation of the pulse wave analysis index; and
    an output unit that outputs the calculated pulse wave analysis index as an analysis result and the degree of stability as an index indicating reliability of the pulse wave analysis index.

2. The pulse wave analysis device according to claim 1, wherein
    the storage unit stores the pulse waveform for a plurality of beats for multiple extremities,
    for each of the multiple extremities, the analysis processing unit integrates the pulse waveform shapes of each beat and calculates the degree of approximation, the pulse wave analysis index, and the degree of stability, and
    the output unit outputs, as the analysis result, the pulse wave analysis index corresponding to an extremity for which the degree of stability is the highest.

3. The pulse wave analysis device according to claim 1, wherein
    the storage unit stores the pulse waveform for a plurality of beats for a left extremity and a right extremity, and
    the analysis processing unit calculates the degree of approximation for each extremity, and calculates the pulse wave analysis index using the pulse waveform shape of the extremity for which the degree of approximation is the highest.

4. The pulse wave analysis device according to claim 1, wherein in calculating the degree of approximation, the analysis processing unit limits the pulse waveform shapes of each beat to a range of the waveform shape that has influence on calculation of the pulse wave analysis index.

5. The pulse wave analysis device according to claim 1, wherein the pulse wave analysis index indicates a degree of arterial sclerosis and/or a degree of blood vessel stenosis.

6. The pulse wave analysis device according to claim 5, wherein the pulse wave analysis index includes a pulse wave velocity as an index indicating the degree of arterial sclerosis.

7. The pulse wave analysis device according to claim 1, further comprising: a pulse wave detection unit configured to detect a pulse wave of an extremity, wherein the analysis processing unit calculates the pulse waveform for a plurality of beats based on a detection signal from the pulse wave detection unit.

8. A non-transitory computer-readable medium having recorded thereon a pulse wave analysis program for causing a computer to function as a device for analyzing a pulse wave, the pulse wave analysis program causing the computer to execute the steps of:

integrating pulse waveform shapes of each beat that constitute a pulse waveform for a plurality of beats that are stored in a storage unit by combining the plurality of beats, so as to obtain an integrated pulse waveform shape;

determining a degree of approximation between the integrated pulse waveform shape and each of the plurality of beats;

calculating a pulse wave analysis index for the plurality of beats after excluding, as a calculation target, a beat for which the degree of approximation between the integrated pulse waveform shape and the pulse waveform shape of the beat is low;

calculating a degree of stability of beating by integrating the degrees of approximation of each pulse waveform shape used in the calculation of the pulse wave analysis index; and outputting the calculated pulse wave analysis index as an analysis result and the degree of stability as an index indicating reliability of the pulse wave analysis.

\* \* \* \* \*